US009865512B2

(12) United States Patent
Jayaraman et al.

(10) Patent No.: US 9,865,512 B2
(45) Date of Patent: Jan. 9, 2018

(54) DYNAMIC DESIGN ATTRIBUTES FOR WAFER INSPECTION

(71) Applicant: KLA-Tencor Corporation, Milpitas, CA (US)

(72) Inventors: Thirupurasundari Jayaraman, Chennai (IN); Raghav Babulnath, San Jose, CA (US)

(73) Assignee: KLA-Tencor Corp., Milpitas, CA (US)

(*) Notice: Subject to any disclaimer, the term of this patent is extended or adjusted under 35 U.S.C. 154(b) by 837 days.

(21) Appl. No.: 14/244,859

(22) Filed: Apr. 3, 2014

(65) Prior Publication Data
US 2014/0303921 A1    Oct. 9, 2014

Related U.S. Application Data

(60) Provisional application No. 61/809,676, filed on Apr. 8, 2013, provisional application No. 61/810,163, filed on Apr. 9, 2013.

(51) Int. Cl.
*G01R 31/265* (2006.01)
*H01L 21/66* (2006.01)
(Continued)

(52) U.S. Cl.
CPC .......... *H01L 22/12* (2013.01); *G01N 21/9501* (2013.01); *G06T 7/001* (2013.01); *G06T 2207/30148* (2013.01)

(58) Field of Classification Search
CPC ...... G01N 21/9501; G06T 2207/30148; G06T 7/0006; G06F 17/5081; H01L 2924/00
See application file for complete search history.

(56) References Cited

U.S. PATENT DOCUMENTS 3,495,269 A    2/1970 Mutschler et al.
3,496,352 A    2/1970 Jugle
(Continued)

FOREIGN PATENT DOCUMENTS

CN    1339140    3/2002
CN    1398348    2/2003
(Continued)

OTHER PUBLICATIONS

Gu et al., "Lossless Compression Algorithms for Hierarchical IC Layout," IEEE Transactions on Semiconductor Manufacturing, vol. 21, No. 2, May 2008, pp. 285-296.
(Continued)

*Primary Examiner* — John Breene
*Assistant Examiner* — Mohammad Islam
(74) *Attorney, Agent, or Firm* — Ann Marie Mewherter

(57) ABSTRACT

Methods and systems for dynamic design attributes for wafer inspection are provided. One method includes, at run time of a wafer inspection recipe, prompting a user of a wafer inspection tool on which the wafer inspection recipe is performed for information for a design based binning (DBB) process. The information includes one or more formulae for calculating design attributes from a design for a wafer. The design attributes are used to bin the defects in the DBB process. The method also includes performing inspection of a wafer according to an updated wafer inspection recipe. Performing the inspection includes binning defects detected on the wafer according to the DBB process in the updated wafer inspection recipe.

33 Claims, 7 Drawing Sheets

(51) Int. Cl.
G06T 7/00 (2017.01)
G01N 21/95 (2006.01)

(56) References Cited

U.S. PATENT DOCUMENTS

| | | | |
|---|---|---|---|
| 3,909,602 A | 9/1975 | Micka |
| 4,015,203 A | 3/1977 | Verkuil |
| 4,247,203 A | 1/1981 | Levy et al. |
| 4,347,001 A | 8/1982 | Levy et al. |
| 4,378,159 A | 3/1983 | Galbraith |
| 4,448,532 A | 5/1984 | Joseph et al. |
| 4,475,122 A | 10/1984 | Green |
| 4,532,650 A | 7/1985 | Wihl et al. |
| 4,555,798 A | 11/1985 | Broadbent, Jr. et al. |
| 4,578,810 A | 3/1986 | MacFarlane et al. |
| 4,579,455 A | 4/1986 | Levy et al. |
| 4,595,289 A | 6/1986 | Feldman et al. |
| 4,599,558 A | 7/1986 | Castellano, Jr. et al. |
| 4,633,504 A | 12/1986 | Wihl |
| 4,641,353 A | 2/1987 | Kobayashi |
| 4,641,967 A | 2/1987 | Pecen |
| 4,734,721 A | 3/1988 | Boyer et al. |
| 4,748,327 A | 5/1988 | Shinozaki et al. |
| 4,758,094 A | 7/1988 | Wihl et al. |
| 4,766,324 A | 8/1988 | Saadat et al. |
| 4,799,175 A | 1/1989 | Sano et al. |
| 4,805,123 A | 2/1989 | Specht et al. |
| 4,812,756 A | 3/1989 | Curtis et al. |
| 4,814,829 A | 3/1989 | Kosugi et al. |
| 4,817,123 A | 3/1989 | Sones et al. |
| 4,845,558 A | 7/1989 | Tsai et al. |
| 4,877,326 A | 10/1989 | Chadwick et al. |
| 4,926,489 A | 5/1990 | Danielson et al. |
| 4,928,313 A | 5/1990 | Leonard et al. |
| 5,046,109 A | 9/1991 | Fujimori et al. |
| 5,124,927 A | 6/1992 | Hopewell et al. |
| 5,189,481 A | 2/1993 | Jann et al. |
| 5,355,212 A | 10/1994 | Wells et al. |
| 5,444,480 A | 8/1995 | Sumita |
| 5,453,844 A | 9/1995 | George et al. |
| 5,481,624 A | 1/1996 | Kamon |
| 5,485,091 A | 1/1996 | Verkuil |
| 5,497,381 A | 3/1996 | O'Donoghue et al. |
| 5,528,153 A | 6/1996 | Taylor et al. |
| 5,544,256 A | 8/1996 | Brecher et al. |
| 5,563,702 A | 10/1996 | Emery et al. |
| 5,572,598 A | 11/1996 | Wihl et al. |
| 5,578,821 A | 11/1996 | Meisberger et al. |
| 5,594,247 A | 1/1997 | Verkuil et al. |
| 5,608,538 A | 3/1997 | Edgar et al. |
| 5,619,548 A | 4/1997 | Koppel |
| 5,621,519 A | 4/1997 | Frost et al. |
| 5,644,223 A | 7/1997 | Verkuil |
| 5,650,731 A | 7/1997 | Fung et al. |
| 5,661,408 A | 8/1997 | Kamieniecki et al. |
| 5,689,614 A | 11/1997 | Gronet et al. |
| 5,694,478 A | 12/1997 | Braier et al. |
| 5,696,835 A | 12/1997 | Hennessey et al. |
| 5,703,969 A | 12/1997 | Hennessey et al. |
| 5,716,889 A | 2/1998 | Tsuji et al. |
| 5,737,072 A | 4/1998 | Emery et al. |
| 5,742,658 A | 4/1998 | Tiffin et al. |
| 5,754,678 A | 5/1998 | Hawthorne et al. |
| 5,767,691 A | 6/1998 | Verkuil |
| 5,767,693 A | 6/1998 | Verkuil |
| 5,771,317 A | 6/1998 | Edgar |
| 5,773,989 A | 6/1998 | Edelman et al. |
| 5,774,179 A | 6/1998 | Chevrette et al. |
| 5,795,685 A | 8/1998 | Liebmann et al. |
| 5,822,218 A | 10/1998 | Moosa et al. |
| 5,831,865 A | 11/1998 | Berezin et al. |
| 5,834,941 A | 11/1998 | Verkuil |
| 5,852,232 A | 12/1998 | Samsavar et al. |
| 5,866,806 A | 2/1999 | Samsavar et al. |
| 5,874,733 A | 2/1999 | Silver et al. |
| 5,884,242 A | 3/1999 | Meier et al. |
| 5,889,593 A | 3/1999 | Bareket |
| 5,917,332 A | 6/1999 | Chen et al. |
| 5,932,377 A | 8/1999 | Ferguson et al. |
| 5,940,458 A | 8/1999 | Suk |
| 5,948,972 A | 9/1999 | Samsavar et al. |
| 5,955,661 A | 9/1999 | Samsavar et al. |
| 5,965,306 A | 10/1999 | Mansfield et al. |
| 5,978,501 A | 11/1999 | Badger et al. |
| 5,980,187 A | 11/1999 | Verhovsky |
| 5,986,263 A | 11/1999 | Hiroi et al. |
| 5,991,699 A | 11/1999 | Kulkarni et al. |
| 5,999,003 A | 12/1999 | Steffan et al. |
| 6,011,404 A | 1/2000 | Ma et al. |
| 6,014,461 A | 1/2000 | Hennessey et al. |
| 6,040,911 A | 3/2000 | Nozaki et al. |
| 6,040,912 A | 3/2000 | Zika et al. |
| 6,052,478 A | 4/2000 | Wihl et al. |
| 6,060,709 A | 5/2000 | Verkuil et al. |
| 6,072,320 A | 6/2000 | Verkuil |
| 6,076,465 A | 6/2000 | Vacca et al. |
| 6,078,738 A | 6/2000 | Garza et al. |
| 6,091,257 A | 7/2000 | Verkuil et al. |
| 6,091,846 A | 7/2000 | Lin et al. |
| 6,097,196 A | 8/2000 | Verkuil et al. |
| 6,097,887 A | 8/2000 | Hardikar et al. |
| 6,104,206 A | 8/2000 | Verkuil |
| 6,104,835 A | 8/2000 | Han |
| 6,117,598 A | 9/2000 | Imai |
| 6,121,783 A | 9/2000 | Horner et al. |
| 6,122,017 A | 9/2000 | Taubman |
| 6,122,046 A | 9/2000 | Almogy |
| 6,137,570 A | 10/2000 | Chuang et al. |
| 6,141,038 A | 10/2000 | Young et al. |
| 6,146,627 A | 11/2000 | Muller et al. |
| 6,171,737 B1 | 1/2001 | Phan et al. |
| 6,175,645 B1 | 1/2001 | Elyasaf et al. |
| 6,184,929 B1 | 2/2001 | Noda et al. |
| 6,184,976 B1 | 2/2001 | Park et al. |
| 6,191,605 B1 | 2/2001 | Miller et al. |
| 6,201,999 B1 | 3/2001 | Jevtic |
| 6,202,029 B1 | 3/2001 | Verkuil et al. |
| 6,205,239 B1 | 3/2001 | Lin et al. |
| 6,215,551 B1 | 4/2001 | Nikoonahad et al. |
| 6,224,638 B1 | 5/2001 | Jevtic et al. |
| 6,233,719 B1 | 5/2001 | Hardikar et al. |
| 6,246,787 B1 | 6/2001 | Hennessey et al. |
| 6,248,485 B1 | 6/2001 | Cuthbert |
| 6,248,486 B1 | 6/2001 | Dirksen et al. |
| 6,259,960 B1 | 7/2001 | Inokuchi |
| 6,266,437 B1 | 7/2001 | Eichel et al. |
| 6,267,005 B1 | 7/2001 | Samsavar et al. |
| 6,268,093 B1 | 7/2001 | Kenan et al. |
| 6,272,236 B1 | 8/2001 | Pierrat et al. |
| 6,282,309 B1 | 8/2001 | Emery |
| 6,292,582 B1 | 9/2001 | Lin et al. |
| 6,295,374 B1 | 9/2001 | Robinson et al. |
| 6,324,298 B1 | 11/2001 | O'Dell et al. |
| 6,336,082 B1 | 1/2002 | Nguyen et al. |
| 6,344,640 B1 | 2/2002 | Rhoads |
| 6,363,166 B1 | 3/2002 | Wihl et al. |
| 6,366,687 B1 | 4/2002 | Aloni et al. |
| 6,373,975 B1 | 4/2002 | Bula et al. |
| 6,388,747 B2 | 5/2002 | Nara et al. |
| 6,393,602 B1 | 5/2002 | Atchison et al. |
| 6,407,373 B1 | 6/2002 | Dotan |
| 6,415,421 B2 | 7/2002 | Anderson et al. |
| 6,427,024 B1 | 7/2002 | Bishop |
| 6,445,199 B1 | 9/2002 | Satya et al. |
| 6,451,690 B1 | 9/2002 | Matsumoto et al. |
| 6,459,520 B1 | 10/2002 | Takayama |
| 6,466,314 B1 | 10/2002 | Lehman |
| 6,466,315 B1 | 10/2002 | Karpol et al. |
| 6,470,489 B1 | 10/2002 | Chang et al. |
| 6,483,938 B1 | 11/2002 | Hennessey et al. |
| 6,513,151 B1 | 1/2003 | Erhardt et al. |
| 6,526,164 B1 | 2/2003 | Mansfield et al. |
| 6,529,621 B1 | 3/2003 | Glasser et al. |
| 6,535,628 B2 | 3/2003 | Smargiassi et al. |

(56) References Cited

U.S. PATENT DOCUMENTS

| | | |
|---|---|---|
| 6,539,106 B1 | 3/2003 | Gallarda et al. |
| 6,553,329 B2 | 4/2003 | Balachandran |
| 6,569,691 B1 | 5/2003 | Jastrzebski et al. |
| 6,581,193 B1 | 6/2003 | McGhee et al. |
| 6,593,748 B1 | 7/2003 | Halliyal et al. |
| 6,597,193 B2 | 7/2003 | Lagowski et al. |
| 6,602,728 B1 | 8/2003 | Liebmann et al. |
| 6,608,681 B2 | 8/2003 | Tanaka et al. |
| 6,614,520 B1 | 9/2003 | Bareket et al. |
| 6,631,511 B2 | 10/2003 | Haffner et al. |
| 6,636,301 B1 | 10/2003 | Kvamme et al. |
| 6,642,066 B1 | 11/2003 | Halliyal et al. |
| 6,658,640 B2 | 12/2003 | Weed |
| 6,665,065 B1 | 12/2003 | Phan et al. |
| 6,670,082 B2 | 12/2003 | Liu et al. |
| 6,680,621 B2 | 1/2004 | Savtchouk |
| 6,691,052 B1 | 2/2004 | Maurer |
| 6,701,004 B1 | 3/2004 | Shykind et al. |
| 6,718,526 B1 | 4/2004 | Eldredge et al. |
| 6,721,695 B1 | 4/2004 | Chen et al. |
| 6,734,696 B2 | 5/2004 | Horner et al. |
| 6,738,954 B1 | 5/2004 | Allen et al. |
| 6,748,103 B2 | 6/2004 | Glasser et al. |
| 6,751,519 B1 | 6/2004 | Satya et al. |
| 6,753,954 B2 | 6/2004 | Chen |
| 6,757,645 B2 | 6/2004 | Chang et al. |
| 6,759,655 B2 | 7/2004 | Nara et al. |
| 6,771,806 B1 | 8/2004 | Satya et al. |
| 6,775,818 B2 | 8/2004 | Taravade et al. |
| 6,777,147 B1 | 8/2004 | Fonseca et al. |
| 6,777,676 B1 | 8/2004 | Wang et al. |
| 6,778,695 B1 | 8/2004 | Schellenberg et al. |
| 6,779,159 B2 | 8/2004 | Yokoyama et al. |
| 6,784,446 B1 | 8/2004 | Phan et al. |
| 6,788,400 B2 | 9/2004 | Chen |
| 6,789,032 B2 | 9/2004 | Barbour et al. |
| 6,803,554 B2 | 10/2004 | Ye et al. |
| 6,806,456 B1 | 10/2004 | Ye et al. |
| 6,807,503 B2 | 10/2004 | Ye et al. |
| 6,813,572 B2 | 11/2004 | Satya et al. |
| 6,820,028 B2 | 11/2004 | Ye et al. |
| 6,828,542 B2 | 12/2004 | Ye et al. |
| 6,842,225 B1 | 1/2005 | Irie et al. |
| 6,859,746 B1 | 2/2005 | Stirton |
| 6,879,403 B2 | 4/2005 | Freifeld |
| 6,879,924 B2 | 4/2005 | Ye et al. |
| 6,882,745 B2 | 4/2005 | Brankner et al. |
| 6,884,984 B2 | 4/2005 | Ye et al. |
| 6,886,153 B1 | 4/2005 | Bevis |
| 6,892,156 B2 | 5/2005 | Ye et al. |
| 6,902,855 B2 | 6/2005 | Peterson et al. |
| 6,906,305 B2 | 6/2005 | Pease et al. |
| 6,918,101 B1 | 7/2005 | Satya et al. |
| 6,919,957 B2 | 7/2005 | Nikoonahad et al. |
| 6,937,753 B1 | 8/2005 | O'Dell et al. |
| 6,948,141 B1 | 9/2005 | Satya et al. |
| 6,959,255 B2 | 10/2005 | Ye et al. |
| 6,966,047 B1 | 11/2005 | Glasser |
| 6,969,837 B2 | 11/2005 | Ye et al. |
| 6,969,864 B2 | 11/2005 | Ye et al. |
| 6,983,060 B1 | 1/2006 | Martinent-Catalot et al. |
| 6,988,045 B2 | 1/2006 | Purdy |
| 6,990,385 B1 | 1/2006 | Smith et al. |
| 7,003,755 B2 | 2/2006 | Pang et al. |
| 7,003,758 B2 | 2/2006 | Ye et al. |
| 7,012,438 B1 | 3/2006 | Miller et al. |
| 7,026,615 B2 | 4/2006 | Takane et al. |
| 7,027,143 B1 | 4/2006 | Stokowski et al. |
| 7,030,966 B2 | 4/2006 | Hansen |
| 7,030,997 B2 | 4/2006 | Neureuther et al. |
| 7,053,355 B2 | 5/2006 | Ye et al. |
| 7,061,625 B1 | 6/2006 | Hwang et al. |
| 7,071,833 B2 | 7/2006 | Nagano et al. |
| 7,103,484 B1 | 9/2006 | Shi et al. |
| 7,106,895 B1 | 9/2006 | Goldberg et al. |
| 7,107,517 B1 | 9/2006 | Suzuki et al. |
| 7,107,571 B2 | 9/2006 | Chang et al. |
| 7,111,277 B2 | 9/2006 | Ye et al. |
| 7,114,143 B2 | 9/2006 | Hanson et al. |
| 7,114,145 B2 | 9/2006 | Ye et al. |
| 7,117,477 B2 | 10/2006 | Ye et al. |
| 7,117,478 B2 | 10/2006 | Ye et al. |
| 7,120,285 B1 | 10/2006 | Spence |
| 7,120,895 B2 | 10/2006 | Ye et al. |
| 7,123,356 B1 | 10/2006 | Stokowski et al. |
| 7,124,386 B2 | 10/2006 | Smith et al. |
| 7,133,070 B2 | 11/2006 | Wheeler |
| 7,133,548 B2 | 11/2006 | Kenan et al. |
| 7,135,344 B2 | 11/2006 | Nehmadi et al. |
| 7,136,143 B2 | 11/2006 | Smith |
| 7,152,215 B2 | 12/2006 | Smith et al. |
| 7,162,071 B2 | 1/2007 | Hung et al. |
| 7,170,593 B2 | 1/2007 | Honda et al. |
| 7,171,334 B2 | 1/2007 | Gassner |
| 7,174,520 B2 | 2/2007 | White et al. |
| 7,194,709 B2 | 3/2007 | Brankner |
| 7,207,017 B1 | 4/2007 | Tabery et al. |
| 7,231,628 B2 | 6/2007 | Pack et al. |
| 7,236,847 B2 | 6/2007 | Marella |
| 7,271,891 B1 | 9/2007 | Xiong et al. |
| 7,379,175 B1 | 5/2008 | Stokowski et al. |
| 7,383,156 B2 | 6/2008 | Matsusita et al. |
| 7,386,839 B1 | 6/2008 | Golender et al. |
| 7,388,979 B2 | 6/2008 | Sakai et al. |
| 7,418,124 B2 | 8/2008 | Peterson et al. |
| 7,424,145 B2 | 9/2008 | Horie et al. |
| 7,440,093 B1 | 10/2008 | Xiong et al. |
| 7,558,419 B1 | 7/2009 | Ye et al. |
| 7,570,796 B2 | 8/2009 | Zafar et al. |
| 7,676,077 B2 | 3/2010 | Kulkarni et al. |
| 7,683,319 B2 | 3/2010 | Makino et al. |
| 7,738,093 B2 | 6/2010 | Alles et al. |
| 7,739,064 B1 | 6/2010 | Ryker et al. |
| 7,752,584 B2 | 7/2010 | Yang |
| 7,760,929 B2 | 7/2010 | Orbon et al. |
| 7,769,225 B2 | 8/2010 | Kekare et al. |
| 7,774,153 B1 | 8/2010 | Smith |
| 7,877,722 B2 | 1/2011 | Duffy et al. |
| 7,890,917 B1 | 2/2011 | Young et al. |
| 7,904,845 B2 | 3/2011 | Fouquet et al. |
| 7,968,859 B2 | 6/2011 | Young et al. |
| 8,041,103 B2 | 10/2011 | Kulkarni et al. |
| 8,041,106 B2 | 10/2011 | Pak et al. |
| 8,073,240 B2 | 12/2011 | Fischer et al. |
| 8,112,241 B2 | 2/2012 | Xiong |
| 8,126,255 B2 | 2/2012 | Bhaskar et al. |
| 8,204,297 B1 | 6/2012 | Xiong et al. |
| 8,216,773 B1* | 7/2012 | Delgado .......... H01J 61/0737 430/311 |
| 8,223,327 B2 | 7/2012 | Chen et al. |
| 8,255,172 B2 | 8/2012 | Auerbach |
| 8,269,960 B2 | 9/2012 | Reich et al. |
| 8,605,275 B2 | 12/2013 | Chen et al. |
| 2001/0017694 A1 | 8/2001 | Oomori et al. |
| 2001/0019625 A1 | 9/2001 | Kenan et al. |
| 2001/0022858 A1 | 9/2001 | Komiya et al. |
| 2001/0043735 A1 | 11/2001 | Smargiassi et al. |
| 2002/0010560 A1 | 1/2002 | Balachandran |
| 2002/0019729 A1 | 2/2002 | Chang et al. |
| 2002/0026626 A1 | 2/2002 | Randall et al. |
| 2002/0033449 A1 | 3/2002 | Nakasuji et al. |
| 2002/0035461 A1 | 3/2002 | Chang et al. |
| 2002/0035641 A1 | 3/2002 | Kurose et al. |
| 2002/0035717 A1 | 3/2002 | Matsuoka |
| 2002/0054291 A1 | 5/2002 | Tsai et al. |
| 2002/0088951 A1 | 7/2002 | Chen |
| 2002/0090746 A1 | 7/2002 | Xu et al. |
| 2002/0134936 A1 | 9/2002 | Matsui et al. |
| 2002/0144230 A1 | 10/2002 | Rittman |
| 2002/0145734 A1 | 10/2002 | Watkins et al. |
| 2002/0164065 A1 | 11/2002 | Cai et al. |
| 2002/0168099 A1 | 11/2002 | Noy |
| 2002/0176096 A1 | 11/2002 | Sentoku et al. |
| 2002/0181756 A1 | 12/2002 | Shibuya et al. |

(56) References Cited

U.S. PATENT DOCUMENTS

| | | |
|---|---|---|
| 2002/0186878 A1 | 12/2002 | Hoon et al. |
| 2002/0192578 A1 | 12/2002 | Tanaka et al. |
| 2003/0004699 A1 | 1/2003 | Choi et al. |
| 2003/0014146 A1 | 1/2003 | Fujii et al. |
| 2003/0017664 A1 | 1/2003 | Pnueli et al. |
| 2003/0022401 A1 | 1/2003 | Hamamatsu et al. |
| 2003/0033046 A1 | 2/2003 | Yoshitake et al. |
| 2003/0048458 A1 | 3/2003 | Mieher et al. |
| 2003/0048939 A1 | 3/2003 | Lehman |
| 2003/0057971 A1 | 3/2003 | Nishiyama et al. |
| 2003/0076989 A1 | 4/2003 | Maayah et al. |
| 2003/0082463 A1 | 5/2003 | Laidig et al. |
| 2003/0086081 A1 | 5/2003 | Lehman |
| 2003/0094572 A1 | 5/2003 | Matsui et al. |
| 2003/0098805 A1 | 5/2003 | Bizjak et al. |
| 2003/0128870 A1 | 7/2003 | Pease et al. |
| 2003/0138138 A1 | 7/2003 | Vacca et al. |
| 2003/0138978 A1 | 7/2003 | Tanaka et al. |
| 2003/0169916 A1 | 9/2003 | Hayashi et al. |
| 2003/0173516 A1 | 9/2003 | Takane et al. |
| 2003/0192015 A1 | 10/2003 | Liu |
| 2003/0207475 A1 | 11/2003 | Nakasuji et al. |
| 2003/0223639 A1 | 12/2003 | Shlain et al. |
| 2003/0226951 A1 | 12/2003 | Ye et al. |
| 2003/0227620 A1 | 12/2003 | Yokoyama et al. |
| 2003/0228050 A1 | 12/2003 | Geshel et al. |
| 2003/0228714 A1 | 12/2003 | Smith et al. |
| 2003/0229410 A1 | 12/2003 | Smith et al. |
| 2003/0229412 A1 | 12/2003 | White et al. |
| 2003/0229868 A1 | 12/2003 | White et al. |
| 2003/0229875 A1 | 12/2003 | Smith et al. |
| 2003/0229880 A1 | 12/2003 | White et al. |
| 2003/0229881 A1 | 12/2003 | White et al. |
| 2003/0237064 A1 | 12/2003 | White et al. |
| 2004/0030430 A1 | 2/2004 | Matsuoka |
| 2004/0032908 A1 | 2/2004 | Hagai et al. |
| 2004/0049722 A1 | 3/2004 | Matsushita |
| 2004/0052411 A1 | 3/2004 | Qian et al. |
| 2004/0057611 A1 | 3/2004 | Lee et al. |
| 2004/0066506 A1 | 4/2004 | Elichai et al. |
| 2004/0091142 A1 | 5/2004 | Peterson et al. |
| 2004/0094762 A1 | 5/2004 | Hess et al. |
| 2004/0098216 A1 | 5/2004 | Ye et al. |
| 2004/0102934 A1 | 5/2004 | Chang |
| 2004/0107412 A1 | 6/2004 | Pack et al. |
| 2004/0119036 A1 | 6/2004 | Ye et al. |
| 2004/0120569 A1 | 6/2004 | Hung et al. |
| 2004/0133369 A1 | 7/2004 | Pack et al. |
| 2004/0147121 A1 | 7/2004 | Nakagaki et al. |
| 2004/0174506 A1 | 9/2004 | Smith |
| 2004/0179738 A1 | 9/2004 | Dai et al. |
| 2004/0199885 A1 | 10/2004 | Lu et al. |
| 2004/0223639 A1 | 11/2004 | Sato et al. |
| 2004/0228515 A1 | 11/2004 | Okabe et al. |
| 2004/0234120 A1 | 11/2004 | Honda et al. |
| 2004/0243320 A1 | 12/2004 | Chang et al. |
| 2004/0246476 A1 | 12/2004 | Bevis et al. |
| 2004/0254752 A1 | 12/2004 | Wisniewski et al. |
| 2005/0004774 A1 | 1/2005 | Volk et al. |
| 2005/0008218 A1 | 1/2005 | O'Dell et al. |
| 2005/0010890 A1 | 1/2005 | Nehmadi et al. |
| 2005/0013474 A1 | 1/2005 | Sim |
| 2005/0062962 A1 | 3/2005 | Fairley et al. |
| 2005/0069217 A1 | 3/2005 | Mukherjee |
| 2005/0117796 A1 | 6/2005 | Matsui et al. |
| 2005/0132306 A1 | 6/2005 | Smith et al. |
| 2005/0141764 A1 | 6/2005 | Tohyama et al. |
| 2005/0166174 A1 | 7/2005 | Ye et al. |
| 2005/0184252 A1 | 8/2005 | Ogawa et al. |
| 2005/0190957 A1 | 9/2005 | Cai et al. |
| 2005/0198602 A1 | 9/2005 | Brankner et al. |
| 2005/0249318 A1 | 11/2005 | Minemura |
| 2006/0000964 A1 | 1/2006 | Ye et al. |
| 2006/0036979 A1 | 2/2006 | Zurbrick et al. |
| 2006/0038986 A1 | 2/2006 | Honda et al. |
| 2006/0048089 A1 | 3/2006 | Schwarzband |
| 2006/0051682 A1 | 3/2006 | Hess et al. |
| 2006/0062445 A1 | 3/2006 | Verma et al. |
| 2006/0066339 A1 | 3/2006 | Rajski et al. |
| 2006/0078192 A1 | 4/2006 | Oh |
| 2006/0082763 A1 | 4/2006 | Teh et al. |
| 2006/0083135 A1 | 4/2006 | Minemura |
| 2006/0159333 A1 | 7/2006 | Ishikawa |
| 2006/0161452 A1 | 7/2006 | Hess |
| 2006/0193506 A1 | 8/2006 | Dorphan et al. |
| 2006/0193507 A1 | 8/2006 | Sali et al. |
| 2006/0236294 A1 | 10/2006 | Saidin et al. |
| 2006/0236297 A1 | 10/2006 | Melvin, III et al. |
| 2006/0239536 A1 | 10/2006 | Shibuya et al. |
| 2006/0265145 A1 | 11/2006 | Huet et al. |
| 2006/0266243 A1 | 11/2006 | Percin et al. |
| 2006/0269120 A1 | 11/2006 | Nehmadi et al. |
| 2006/0273242 A1 | 12/2006 | Hunsche et al. |
| 2006/0273266 A1 | 12/2006 | Preil et al. |
| 2006/0277520 A1* | 12/2006 | Gennari ............ G03F 7/706 716/53 |
| 2006/0291714 A1 | 12/2006 | Wu et al. |
| 2006/0292463 A1 | 12/2006 | Best et al. |
| 2007/0002322 A1 | 1/2007 | Borodovsky et al. |
| 2007/0011628 A1 | 1/2007 | Ouali et al. |
| 2007/0013901 A1 | 1/2007 | Kim et al. |
| 2007/0019171 A1 | 1/2007 | Smith |
| 2007/0019856 A1 | 1/2007 | Furman et al. |
| 2007/0031745 A1 | 2/2007 | Ye et al. |
| 2007/0032896 A1 | 2/2007 | Ye et al. |
| 2007/0035322 A1 | 2/2007 | Kang et al. |
| 2007/0035712 A1 | 2/2007 | Gassner et al. |
| 2007/0035728 A1 | 2/2007 | Kekare et al. |
| 2007/0052963 A1 | 3/2007 | Orbon et al. |
| 2007/0064995 A1 | 3/2007 | Oaki et al. |
| 2007/0133860 A1 | 6/2007 | Lin et al. |
| 2007/0156379 A1 | 7/2007 | Kulkarni et al. |
| 2007/0230770 A1 | 10/2007 | Kulkarni et al. |
| 2007/0248257 A1 | 10/2007 | Bruce et al. |
| 2007/0280527 A1 | 12/2007 | Almogy et al. |
| 2007/0288219 A1* | 12/2007 | Zafar ............ G03F 1/84 703/14 |
| 2008/0013083 A1 | 1/2008 | Kirk et al. |
| 2008/0015802 A1 | 1/2008 | Urano et al. |
| 2008/0016481 A1 | 1/2008 | Matsuoka et al. |
| 2008/0018887 A1 | 1/2008 | Chen et al. |
| 2008/0049994 A1 | 2/2008 | Rognin et al. |
| 2008/0058977 A1 | 3/2008 | Honda |
| 2008/0072207 A1 | 3/2008 | Verma et al. |
| 2008/0081385 A1 | 4/2008 | Marella et al. |
| 2008/0163140 A1 | 7/2008 | Fouquet et al. |
| 2008/0167829 A1 | 7/2008 | Park et al. |
| 2008/0250384 A1* | 10/2008 | Duffy ............ G03F 7/7065 716/55 |
| 2008/0295047 A1 | 11/2008 | Nehmadi et al. |
| 2008/0295048 A1 | 11/2008 | Nehmadi et al. |
| 2008/0304056 A1 | 12/2008 | Alles et al. |
| 2009/0024967 A1 | 1/2009 | Su et al. |
| 2009/0037134 A1 | 2/2009 | Kulkarni et al. |
| 2009/0041332 A1 | 2/2009 | Bhaskar et al. |
| 2009/0043527 A1 | 2/2009 | Park et al. |
| 2009/0055783 A1* | 2/2009 | Florence ........ G01R 31/318314 716/136 |
| 2009/0067703 A1 | 3/2009 | Lin et al. |
| 2009/0080759 A1 | 3/2009 | Bhaskar et al. |
| 2009/0210183 A1 | 8/2009 | Rajski et al. |
| 2009/0257645 A1 | 10/2009 | Chen et al. |
| 2009/0284733 A1 | 11/2009 | Wallingford et al. |
| 2009/0290782 A1 | 11/2009 | Regensburger |
| 2009/0299681 A1 | 12/2009 | Chen et al. |
| 2009/0310864 A1 | 12/2009 | Takagi et al. |
| 2009/0323052 A1 | 12/2009 | Silberstein et al. |
| 2010/0076699 A1 | 3/2010 | Auerbach |
| 2010/0142800 A1 | 6/2010 | Pak et al. |
| 2010/0146338 A1 | 6/2010 | Schalick et al. |
| 2010/0150429 A1 | 6/2010 | Jau et al. |
| 2010/0188657 A1 | 7/2010 | Chen et al. |
| 2010/0215247 A1* | 8/2010 | Kitamura ............ G06T 7/001 382/149 |

(56) References Cited

U.S. PATENT DOCUMENTS

| | | | |
|---|---|---|---|
| 2010/0226562 A1 | 9/2010 | Wu et al. | |
| 2011/0013825 A1 | 1/2011 | Shibuya et al. | |
| 2011/0052040 A1 | 3/2011 | Kuan | |
| 2011/0129142 A1 | 6/2011 | Takahashi et al. | |
| 2011/0184662 A1 | 7/2011 | Badger et al. | |
| 2011/0188733 A1 | 8/2011 | Bardos et al. | |
| 2011/0224932 A1 | 9/2011 | Huet et al. | |
| 2011/0251713 A1 | 10/2011 | Teshima et al. | |
| 2011/0276935 A1 | 11/2011 | Fouquet et al. | |
| 2011/0311126 A1 | 12/2011 | Sakai et al. | |
| 2011/0320149 A1* | 12/2011 | Lee | G01N 21/9501 702/83 |
| 2012/0229618 A1 | 9/2012 | Urano et al. | |
| 2012/0308112 A1 | 12/2012 | Hu et al. | |
| 2012/0316855 A1* | 12/2012 | Park | G01N 21/9501 703/13 |
| 2012/0319246 A1 | 12/2012 | Tan et al. | |
| 2013/0009989 A1 | 1/2013 | Chen et al. | |
| 2013/0027196 A1 | 1/2013 | Yankun et al. | |
| 2013/0064442 A1 | 3/2013 | Chang et al. | |
| 2013/0129189 A1 | 5/2013 | Wu et al. | |
| 2013/0236084 A1 | 9/2013 | Li et al. | |
| 2013/0336575 A1 | 12/2013 | Dalla-Torre et al. | |
| 2014/0002632 A1 | 1/2014 | Lin et al. | |
| 2014/0050389 A1 | 2/2014 | Mahadevan et al. | |
| 2014/0185919 A1 | 7/2014 | Lang et al. | |
| 2014/0193065 A1 | 7/2014 | Chu et al. | |
| 2014/0219544 A1 | 8/2014 | Wu et al. | |
| 2014/0241610 A1* | 8/2014 | Duffy | G01N 21/9501 382/149 |

FOREIGN PATENT DOCUMENTS

| | | |
|---|---|---|
| CN | 1646896 | 7/2005 |
| CN | 101275920 | 10/2008 |
| EP | 0032197 | 7/1981 |
| EP | 0370322 | 5/1990 |
| EP | 1061358 | 12/2000 |
| EP | 1061571 | 12/2000 |
| EP | 1065567 | 1/2001 |
| EP | 1066925 | 1/2001 |
| EP | 1069609 | 1/2001 |
| EP | 1093017 | 4/2001 |
| EP | 1329771 | 7/2003 |
| EP | 1480034 | 11/2004 |
| EP | 1696270 | 8/2006 |
| JP | 7-159337 | 6/1995 |
| JP | 2002-071575 | 3/2002 |
| JP | 2002-365235 | 12/2002 |
| JP | 2003-215060 | 7/2003 |
| JP | 2004-045066 | 2/2004 |
| JP | 2005-283326 | 10/2005 |
| JP | 2007-234798 | 9/2007 |
| JP | 2009-122046 | 6/2009 |
| JP | 2010-256242 | 11/2010 |
| JP | 2012-225768 | 11/2012 |
| KR | 10-2001-0007394 | 1/2001 |
| KR | 10-2001-0037026 | 5/2001 |
| KR | 10-2001-0101697 | 11/2001 |
| KR | 10-2003-0055848 | 7/2003 |
| KR | 10-2006-0075691 | 7/2005 |
| KR | 10-2005-0092053 | 9/2005 |
| KR | 10-2006-0124514 | 12/2006 |
| KR | 10-0696276 | 3/2007 |
| KR | 10-2010-0061018 | 6/2010 |
| KR | 10-2012-0068128 | 6/2012 |
| TW | 201128183 | 8/2011 |
| WO | 1998/057358 | 12/1998 |
| WO | 1999/022310 | 5/1999 |
| WO | 1999/025004 | 5/1999 |
| WO | 1999/059200 | 5/1999 |
| WO | 1999/038002 | 7/1999 |
| WO | 1999/041434 | 8/1999 |
| WO | 2000/003234 | 1/2000 |
| WO | 2000/036525 | 6/2000 |
| WO | 2000/055799 | 9/2000 |
| WO | 2000/068884 | 11/2000 |
| WO | 2000/070332 | 11/2000 |
| WO | 2001/009566 | 2/2001 |
| WO | 2001/040145 | 6/2001 |
| WO | 2003/104921 | 12/2003 |
| WO | 2004/027684 | 4/2004 |
| WO | 2004/097903 | 11/2004 |
| WO | 2006/012388 | 2/2006 |
| WO | 2006/063268 | 6/2006 |
| WO | 2009/152046 | 9/2009 |
| WO | 2010/093733 | 8/2010 |

OTHER PUBLICATIONS

International Search Report and Written Opinion for PCT/US2014/033225 dated Jul. 30, 2014.

U.S. Appl. No. 60/681,095, filed May 13, 2005 by Nehmadi et al.

U.S. Appl. No. 60/684,360, filed May 24, 2005 by Nehmadi et al.

U.S. Appl. No. 13/652,377, filed Oct. 15, 2012 by Wu et al.

Allan et al., "Critical Area Extraction for Soft Fault Estimation," IEEE Transactions on Semiconductor Manufacturing, vol. 11, No. 1, Feb. 1998.

Barty et al., "Aerial Image Microscopes for the inspection of defects in EUV masks," Proceedings of SPIE, vol. 4889, 2002, pp. 1073-1084.

Budd et al., "A New Mask Evaluation Tool, the Microlithography Simulation Microscope Aerial Image Measurement System," SPIE vol. 2197, 1994, pp. 530-540.

Cai et al., "Enhanced Dispositioning of Reticle Defects Using the Virtual Stepper With Automoated Defect Severity Scoring," Proceedings of the SPIE, vol. 4409, Jan. 2001, pp. 467-478.

Comizzoli, "Uses of Corona Discharges in the Semiconductor Industry," J. Electrochem. Soc., 1987, pp. 424-429.

Contactless Electrical Equivalent Oxide Thickness Measurement, IBM Technical Disclosure Bulletin, vol. 29, No. 10, 1987, pp. 4622-4623.

Contactless Photovoltage vs. Bias Method for Determining Flat-Band Voltage, IBM Technical Disclosure Bulletin, vol. 32, vol. 9A, 1990, pp. 14-17.

Cosway et al., "Manufacturing Implementation of Corona Oxide Silicon (COS) Systems for Diffusion Furnace Contamination Monitoring," 1997 IEEE/SEMI Advanced Semiconductor Manufacturing Conference, pp. 98-102.

Diebold et al., "Characterization and produiction metrology of thin transistor gate oxide films," Materials Science in Semiconductor Processing 2, 1999, pp. 103-147.

Dirksen et al., "Impact of high order aberrations on the performance of the aberration monitor," Proc. of SPIE vol. 4000, Mar. 2000, pp. 9-17.

Dirksen et al., "Novel aberration monitor for optical lithography," Proc. of SPIE vol. 3679, Jul. 1999, pp. 77-86.

Garcia et al., "New Die to Database Inspection Algorithm for Inspection of 90-nm Node Reticles," Proceedings of SPIE, vol. 5130, 2003, pp. 364-374.

Granik et al., "Sub-resolution process windows and yield estimation technique based on detailed full-chip CD simulation," Mentor Graphics, Sep. 2000, 5 pages.

Hess et al., "A Novel Approach: High Resolution Inspection with Wafer Plane Defect Detection," Proceedings of SPIE—International Society for Optical Engineering; Photomask and Next-Generation Lithography Mask Technology 2008, vol. 7028, 2008.

Huang et al., "Process Window Impact of Progressive Mask Defects, Its Inspection and Disposition Techniques (go/no-go criteria) Via a Lithographic Detector," Proceedings of SPIE—The International Society for Optical Engineering; 25th Annual Bacus Symposium on Photomask Technology 2005, vol. 5992, No. 1, 2005, p. 6.

Huang et al., "Using Design Based Binning to Improve Defect Excursion Control for 45nm Production," IEEE, International Symposium on Semiconductor Manufacturing, Oct. 2007, pp. 1-3.

(56) References Cited

OTHER PUBLICATIONS

Hung et al., Metrology Study of Sub 20 Angstrom oxynitride by Corona-Oxide-Silicon (COS) and Conventional C-V Approaches, 2002, Mat. Res. Soc. Symp. Proc., vol. 716, pp. 119-124.
Karklin et al., "Automatic Defect Severity Scoring for 193 nm Reticle Defect Inspection," Proceedings of SPIE—The International Society for Optical Engineering, 2001, vol. 4346, No. 2, pp. 898-906.
Lo et al., "Identifying Process Window Marginalities of Reticle Designs for 0.15/0.13 μm Technologies," Proceedings of SPIE vol. 5130, 2003, pp. 829-837.
Lorusso et al. "Advanced DFM Applns. Using design-based metrology on CDSEM," SPIE vol. 6152, Mar. 27, 2006.
Lu et al., "Application of Simulation Based Defect Printability Analysis for Mask Qualification Control," Proceedings of SPIE, vol. 5038, 2003, pp. 33-40.
Mack, "Lithographic Simulation: A Review," Proceedings of SPIE vol. 4440, 2001, pp. 59-72.
Martino et al., "Application of the Aerial Image Measurement System (AIMS(TM)) to the Analysis of Binary Mask Imaging and Resolution Enhancement Techniques," SPIE vol. 2197, 1994, pp. 573-584.
Miller, "A New Approach for Measuring Oxide Thickness," Semiconductor International, Jul. 1995, pp. 147-148.
Nagpal et al., "Wafer Plane Inspection for Advanced Reticle Defects," Proceedings of SPIE—The International Society for Optical Engineering; Photomask and Next-Generation Lithography Mask Technology. vol. 7028, 2008.
Numerical Recipes in C. The Art of Scientific Computing, 2nd Ed.,© Cambridge University Press 1988, 1992, p. 683.
O'Gorman et al., "Subpixel Registration Using a Concentric Ring Fiducial," Proceedings of the International Conference on Pattern Recognition, vol. ii, Jun. 16, 1990, pp. 249-253.
Otsu, "A Threshold Selection Method from Gray-Level Histograms," IEEE Transactions on Systems, Man, and Cybernetics, vol. SMC-9, No. 1, Jan. 1979, pp. 62-66.
Pang et al., "Simulation-based Defect Printability Analysis on Alternating Phase Shifting Masks for 193 nm Lithography," Proceedings of SPIE, vol. 4889, 2002, pp. 947-954.
Pettibone et al., "Wafer Printability Simulation Accuracy Based on UV Optical Inspection Images of Reticle Defects," Proceedings of SPIE—The International Society for Optical Engineering 1999 Society of Photo-Optical Instrumentation Engineers, vol. 3677, No. II, 1999, pp. 711-720.
Phan et al., "Comparison of Binary Mask Defect Printability Analysis Using Virtual Stepper System and Aerial Image Microscope System," Proceedings of SPIE—The International Society for Optical Engineering 1999 Society of Photo-Optical Instrumentation Engineers, vol. 3873, 1999, pp. 681-692.
Sahouria et al., "Full-chip Process Simulation for Silicon DRC," Mentor Graphics, Mar. 2000, 6 pages.
Sato et al., "Defect Criticality Index (DCI): A new methodology to significantly improve DOI sampling rate in a 45nm production environment," Metrology, Inspection, and Process Control for Microlithography XXII, Proc. of SPIE vol. 6922, 692213 (2008), pp. 1-9.
Schroder et al., Corona-Oxide-Semiconductor Device Characterization, 1998, Solid-State Electronics, vol. 42, No. 4, pp. 505-512.
Schroder, "Surface voltage and surface photovoltage: history, theory and applications," Measurement Science and Technology, vol. 12, 2001, pp. R16-R31.
Schroder, Contactless Surface Charge Semiconductor Characterization, Apr. 2002, Materials Science and Engineering B, vol. 91-92, pp. 196-228.
Schurz et al., "Simulation Study of Reticle Enhancement Technology Applications for 157 nm Lithography," SPIE vol. 4562, 2002, pp. 902-913.
Svidenko et al. "Dynamic Defect-Limited Yield Prediction by Criticality Factor," ISSM Paper: YE-O-157, 2007.
Tang et al., "Analyzing Volume Diagnosis Results with Statistical Learning for Yield Improvement" 12th IEEE European Test Symposium, Freiburg 2007, IEEE European, May 20-24, 2007, pp. 145-150.
Verkuil et al., "A Contactless Alternative to MOS Charge Measurements by Means of a Corona-Oxide-Semiconductor (COS) Technique,"Electrochem. Soc. Extended Abstracts, 1988, vol. 88-1, No. 169, pp. 261-262.
Verkuil, "Rapid Contactless Method for Measuring Fixed Oxide Charge Associated with Silicon Processing," IBM Technical Disclosure Bulletin, vol. 24, No. 6, 1981, pp. 3048-3053.
Volk et al. "Investigation of Reticle Defect Formation at DUV Lithography," 2002, BACUS Symposium on Photomask Technology.
Volk et al. "Investigation of Reticle Defect Formation at DUV Lithography," 2003, IEEE/SEMI Advanced Manufacturing Conference, pp. 29-35.
Volk et al., "Investigation of Smart Inspection of Critical Layer Reticles using Additional Designer Data to Determine Defect Significance," Proceedings of SPIE vol. 5256, 2003, pp. 489-499.
Weinberg, "Tunneling of Electrons from Si into Thermally Grown SiO2," Solid-State Electronics, 1977, vol. 20, pp. 11-18.
Weinzierl et al., "Non-Contact Corona-Based Process Control Measurements: Where We've Been, Where We're Headed," Electrochemical Society Proceedings, Oct. 1999, vol. 99-16, pp. 342-350.
Yan et al., "Printability of Pellicle Defects in DUV 0.5 um Lithography," SPIE vol. 1604, 1991, pp. 106-117.
Guo et al., "License Plate Localization and Character Segmentation with Feedback Self-Learning and Hybrid Binarization Techniques," IEEE Transactions on Vehicular Technology, vol. 57, No. 3, May 2008, pp. 1417-1424.
Liu, "Robust Image Segmentation Using Local Median," Proceedings of the 3rd Canadian Conference on Computer and Robot Vision (CRV'06) 0-7695-2542-3/06, 2006 IEEE, 7 pages total.

\* cited by examiner

DYNAMIC DESIGN ATTRIBUTES FOR WAFER INSPECTION

BACKGROUND OF THE INVENTION

1. Field of the Invention

This invention generally relates to dynamic design attributes for wafer inspection.

2. Description of the Related Art

The following description and examples are not admitted to be prior art by virtue of their inclusion in this section.

An integrated circuit (IC) design may be developed using a method or system such as electronic design automation (EDA), computer aided design (CAD), and other IC design software. Such methods and systems may be used to generate the circuit pattern database from the IC design. The circuit pattern database includes data representing a plurality of layouts for various layers of the IC. Data in the circuit pattern database may be used to determine layouts for a plurality of reticles. A layout of a reticle generally includes a plurality of polygons that define features in a pattern on the reticle. Each reticle is used to fabricate one of the various layers of the IC. The layers of the IC may include, for example, a junction pattern in a semiconductor substrate, a gate dielectric pattern, a gate electrode pattern, a contact pattern in an interlevel dielectric, and an interconnect pattern on a metallization layer.

The term "design data" as used herein generally refers to the physical design (layout) of an IC and data derived from the physical design through complex simulation or simple geometric and Boolean operations.

Fabricating semiconductor devices such as logic and memory devices typically includes processing a substrate such as a semiconductor wafer using a large number of semiconductor fabrication processes to form various features and multiple levels of the semiconductor devices. For example, lithography is a semiconductor fabrication process that involves transferring a pattern from a reticle to a resist arranged on a semiconductor wafer. Additional examples of semiconductor fabrication processes include, but are not limited to, chemical-mechanical polishing (CMP), etch, deposition, and ion implantation. Multiple semiconductor devices may be fabricated in an arrangement on a single semiconductor wafer and then separated into individual semiconductor devices.

Inspection processes are used at various steps during a semiconductor manufacturing process to detect defects on wafers to promote higher yield in the manufacturing process and thus higher profits. Inspection has always been an important part of fabricating semiconductor devices such as ICs. However, as the dimensions of semiconductor devices decrease, inspection becomes even more important to the successful manufacture of acceptable semiconductor devices because smaller defects can cause the devices to fail.

As design rules shrink, however, semiconductor manufacturing processes may be operating closer to the limitations on the performance capability of the processes. In addition, smaller defects can have an impact on the electrical parameters of the device as the design rules shrink, which drives more sensitive inspections. Therefore, as design rules shrink, the population of potentially yield relevant defects detected by inspection grows dramatically, and the population of nuisance defects detected by inspection also increases dramatically. Therefore, more and more defects may be detected on the wafers, and correcting the processes to eliminate all of the defects may be difficult and expensive.

In trying to maximize the sensitivity of the inspection system to capture subtle spatially systematic "design-for-manufacturability" (DFM) defects resulting from design and process interdependencies, the system may be overwhelmed by millions of events in non-critical areas such as CMP fill regions. Detecting such nuisance defects is disadvantageous for a number of reasons. For example, these nuisance events need to be filtered out of the inspection results by post-processing of the inspection data. In addition, nuisance event detection limits the ultimate achievable sensitivity of the inspection system for DFM applications. A high rate of nuisance defect data may also overload the run time data processing capacity of the inspection system thereby reducing throughput and/or causing the loss of data.

Accordingly, it would be advantageous to develop methods and/or systems for wafer inspection-related applications that do not have one or more of the disadvantages described above.

SUMMARY OF THE INVENTION

The following description of various embodiments is not to be construed in any way as limiting the subject matter of the appended claims.

One embodiment relates to a method for wafer inspection. The method includes, at run time of a wafer inspection recipe, prompting a user of a wafer inspection tool on which the wafer inspection recipe is performed for information for a design based binning process. The information includes one or more formulae for calculating design attributes from a design for a wafer. The design attributes are used to bin defects in the design based binning process. The method also includes receiving the information from the user and updating the wafer inspection recipe based on the received information. In addition, the method includes performing inspection of the wafer according to the updated wafer inspection recipe. Performing the inspection includes scanning at least a portion of the wafer with the wafer inspection tool thereby generating output responsive to light from at least a portion of the wafer. Performing the inspection also includes detecting defects on the wafer based on the output. In addition, performing the inspection includes binning the defects detected on the wafer according to the design based binning process in the updated wafer inspection recipe. The prompting, receiving, updating, performing, scanning, detecting, and binning steps are performed by the wafer inspection tool.

The method described above may be performed as described further herein. In addition, the method described above may include any other step(s) of any other method(s) described herein. Furthermore, the method described above may be performed by any of the systems described herein.

Another embodiment relates to a non-transitory computer-readable medium storing program instructions executable on a computer system of a wafer inspection tool for performing a computer-implemented method for wafer inspection. The computer-implemented method includes the steps of the method described above. The computer-readable medium may be further configured as described herein. The steps of the computer-implemented method may be performed as described further herein. In addition, the computer-implemented method for which the program instructions are executable may include any other step(s) of any other method(s) described herein.

An additional embodiment relates to a wafer inspection tool. The wafer inspection tool includes an optical subsystem configured to scan at least a portion of a wafer thereby generating output responsive to light from at least the portion of the wafer. The wafer inspection tool also includes a computer subsystem configured for, at run time of a wafer inspection recipe, prompting a user of the wafer inspection tool on which the wafer inspection recipe is performed for information for a design based binning process. The information includes one or more formulae for calculating design attributes from a design for the wafer. The design attributes are used to bin defects in the design based binning process. The computer subsystem is also configured for receiving the information from the user and updating the wafer inspection recipe based on the received information. In addition, the computer subsystem is configured for detecting defects on the wafer based on the output and binning the defects detected on the wafer according to the design based binning process in the updated wafer inspection recipe. The wafer inspection tool may be further configured as described herein.

BRIEF DESCRIPTION OF THE DRAWINGS

Other objects and advantages of the invention will become apparent upon reading the following detailed description and upon reference to the accompanying drawings in which.

Figure 1:
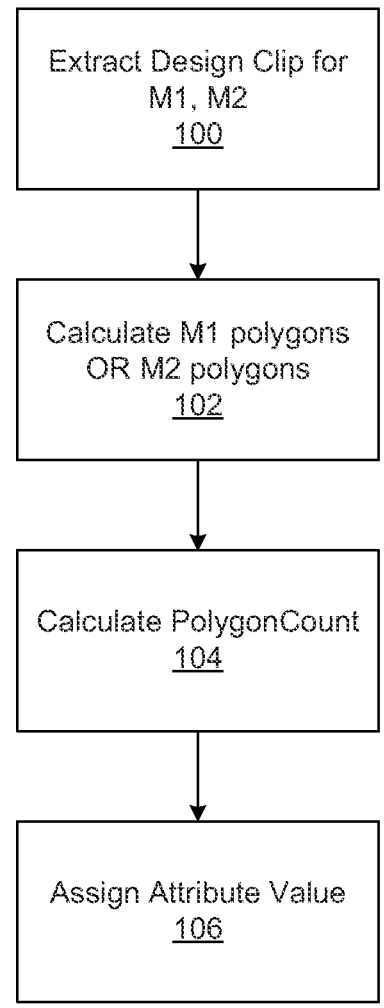
FIG. 1 is a flow chart illustrating embodiment of a method for calculating a design attribute.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals. Unless otherwise noted herein, any of the elements described and shown may include any suitable commercially available elements.

Design based binning (DBB) is a feature that is part of some wafer inspection tools. This feature enables correlating defect locations based on chip design data. This technology has enabled the following use cases on inspection tools:

a) Ability to remove systematic nuisance defects;

b) Systematic defect discovery; and c) Systematic defect classification and monitoring.

For example, design attributes like pattern density and intersection area, which are basically computed based on specific mathematical operations performed on polygonal data, enhance the existing defect attribute paradigm with a rich set of design based information. This design based information is useful in helping bin new nuisance defect types with ease. A "nuisance" or "nuisance defect" is a term commonly used in the art to refer to a potential defect that is detected on a wafer, but that is not an actual defect that is of interest to a user. In this manner, a "nuisance defect" may simply be noise on the wafer that is detected by inspection, which is not representative of any actual defect on the wafer, or an actual defect that the user does not care about.

The only drawback today is that these operations are implemented inside the code as functions. For example, currently, all of the attribute definitions are implemented in the software as functions. The system may implement a set of design based attributes based on predefined operations for one or more layers. If any new attribute needs to be supported, with a new formula, the code has to be modified to introduce new functions. In other words, if new attributes that involve operations are needed, the code must be changed and new calculation logic must be introduced to the software. This requires new software to be released to the field to introduce the new attribute(s). There is no way for the wafer inspection tool user to change the formulae behind the attribute calculation. The customer of the inspection tool can be requested to create the combination data using electronic design automation (EDA). But this again is difficult because of interfacing requirements between design and defect teams.

Figure 7:
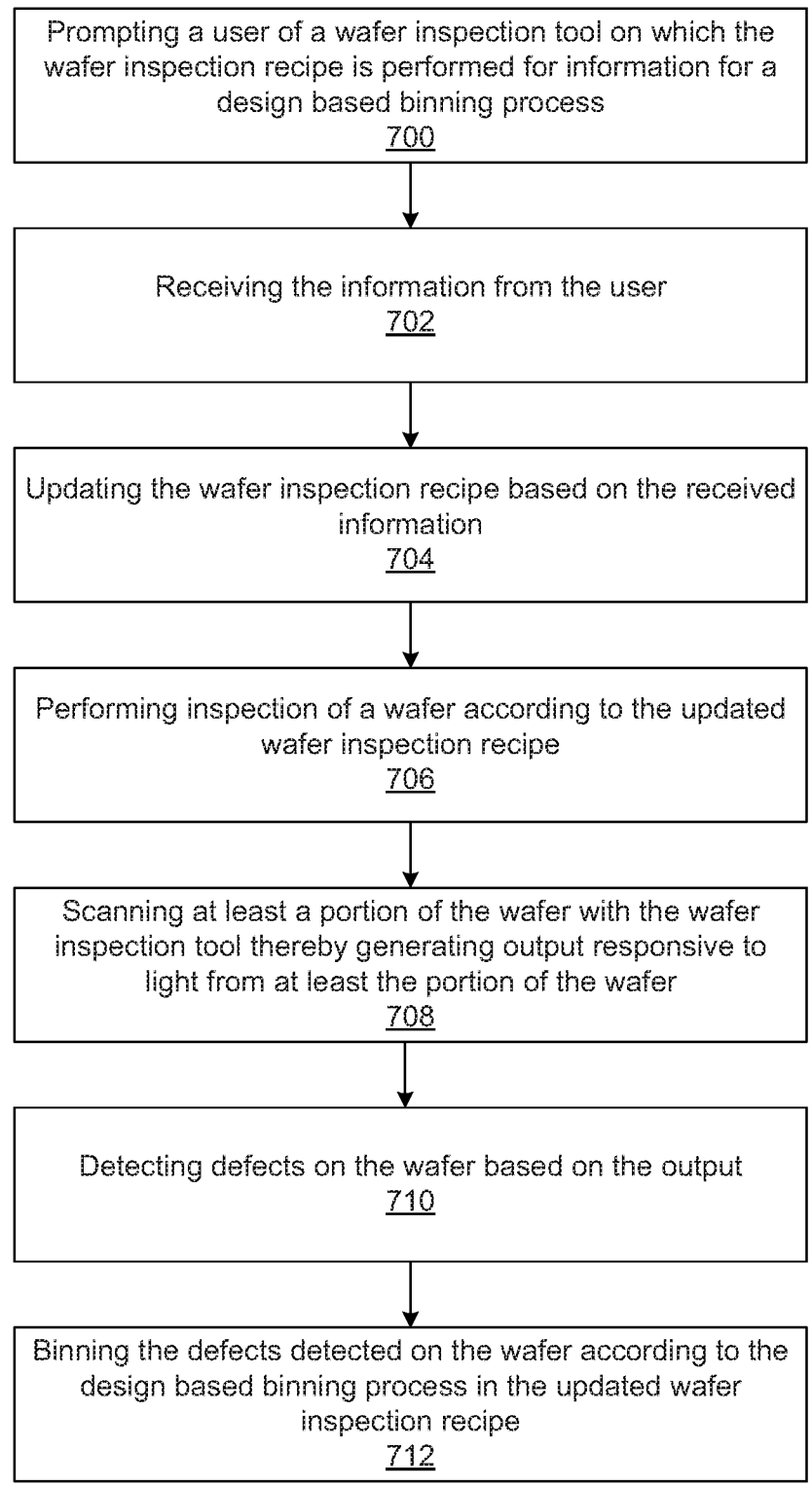
FIG. 7 is a flow diagram illustrating one embodiment of a method for wafer inspection.

One embodiment relates to a method for wafer inspection, as shown in FIG. 7. The embodiments described herein can be used to enhance wafer inspection tools with a new "dynamic design attributes" concept, which can provide the ability to define attribute formulae at run time and use them as part of recipes and other defect sorting and/or classification methods and products such as iDO, which is commercially available from KLA-Tencor, Milpitas, Calif. For example, as shown in step 700, the method includes, at run time of a wafer inspection recipe, prompting a user of a wafer inspection tool on which the wafer inspection recipe is performed for information for a design based binning process. A dynamic design attribute is an extension of an existing design attribute. In addition, the dynamic design attributes described herein may be combined with any existing DBB feature set. In one embodiment, the wafer inspection tool is configured as a broadband plasma tool, one embodiment of which is described further herein.

The information includes one or more formulae for calculating design attributes from a design for a wafer. The design attributes are used to bin defects in the design based binning process. In this manner, the embodiments enable users to define formulae for calculating design attributes. Therefore, the logic behind the calculation of a dynamic design attribute may be obtained from a user of the wafer inspection tool. This way customers and applications engineers can come up with their own formulae based on the interaction between multiple layers of polygons. These formulae can result in different "dynamic design attributes" in the customer's inspection results. The user can add any number of dynamic design attributes. In addition, the embodiments provide users with the flexibility to derive design attribute formulae based on learning in the field. Attributes can be generated on the fly, dynamically. The embodiments described herein are therefore dynamic and have more user control.

The formulae can be applied on "design clips." A "design clip" as that term is used herein is defined as a relatively small portion of the entire design data for the wafer. For example, in one embodiment, the one or more formulae include one or more formulae for calculating the design attributes from portions of design data for the design surrounding locations of the defects detected on the wafer. The portions of the design data surrounding locations of the defects detected on the wafer can be design clips extracted from the entire design data based on the design space coordinates of the defects, which may be determined as described in U.S. Pat. No. 7,570,796 issued on Aug. 4, 2009 to Zafar et al., which is incorporated by reference as if fully set forth herein. In this manner, the attributes can be calculated on the design clips surrounding the defect locations for binning defects effectively.

Information for a dynamic design attribute, some or all of which may be provided by a user, may include an attribute name, an attribute description, an attribute internal name, a calculation formula, which may be one or more formulae described further herein, an attribute datatype, and an attribute value. In one embodiment, the information for the DBB process includes flags for each of the design attributes indicating whether the design attributes are categorical attributes or measurement attributes. A categorical attribute is an attribute that defines a type of the defect and can be expressed as an alphanumeric string. For example, a categorical attribute may be defect types such as bridge defect, particulate defect, and the like. A measurement attribute may be an attribute that defines a dimension of the defect and can be expressed by a value for a measurement or a range of values for the measurement. For example, a measurement attribute may be a range of widths of the defects. In another embodiment, the binning step separates the defects based on portions of design data for the wafer surrounding locations of the defects detected on the wafer, and the information includes flags for each of the design attributes indicating an extent of the portion of the design data used to calculate the design attributes. In one such embodiment, the extent of the portions of the design data are an entirety of the portions of the design data or an area of interest within the portion of the design data. For example, the dynamic design attribute may have a flag indicating whether the attribute is for an entire clip or an extended bounding box (EBB) within the clip. The EBB may represent the area of interest within the design clip. The flags described above may include any suitable indicia that can be used to identify the dynamic design attributes as described above.

An important aspect of the dynamic design attributes described herein is the calculation formulae, which will be described further now. A dynamic design attribute formula may have input that includes the input layer(s). The input layer(s) may include one or more layers of the design for the wafer. A design clip is extracted for these layer(s), and polygons within the clip are used for attribute calculation. In one embodiment, the information includes one or more layer operators for the one or more formulae, and the one or more layer operators are one or more logical operators applied to polygons of two or more layers in the design. For example, a dynamic design attribute formula may also have input that includes a layer operator, which is the logical operator that is applied between two layers. In another embodiment, the information includes one or more calculations for the one or more formulae performed on polygons resulting from the one or more logical operators, and the results of the one or more calculations are the calculated design attributes. For example, a dynamic design attribute formula may have input that includes a result calculator. When a layer operator is applied to input layers of a design clip, a set of polygons may result. A result calculator is then applied on these polygons to arrive at an attribute value. In this manner, the dynamic design attributes described herein provide the ability to combine data from multiple layers using logical operators and tie it to the attribute definition.

In one example of a dynamic design attribute, a design data file may include M1 and M2 layers (for the metal 1 and metal 2 layers of the wafer, respectively). The user can define a dynamic attribute called "MergeCount." MergeCount=POLYGONCOUNT (M1 or M2). The dynamic attribute MergeCount calculation is shown in FIG. 1. In particular, as shown in step 100 of FIG. 1, the calculation includes extracting a design clip for the M and M2 layers, which may be performed as described further herein. The calculation also includes calculating the M1 polygons OR M2 polygons, as shown in step 102 of FIG. 1. As shown in step 104 of FIG. 1, calculating the dynamic attribute further includes calculating PolygonCount. As further shown in step 106, the calculation includes assigning an attribute value, which is performed based on the Polygon-Count result.

In one embodiment, the one or more logical operators include one or more of logical AND, OR, XOR, and NOT operators. For example, in the layer logic operations, part of the calculation formula will be a logical expression between layers using logical AND, OR, XOR, and NOT operators.

Figure 2:
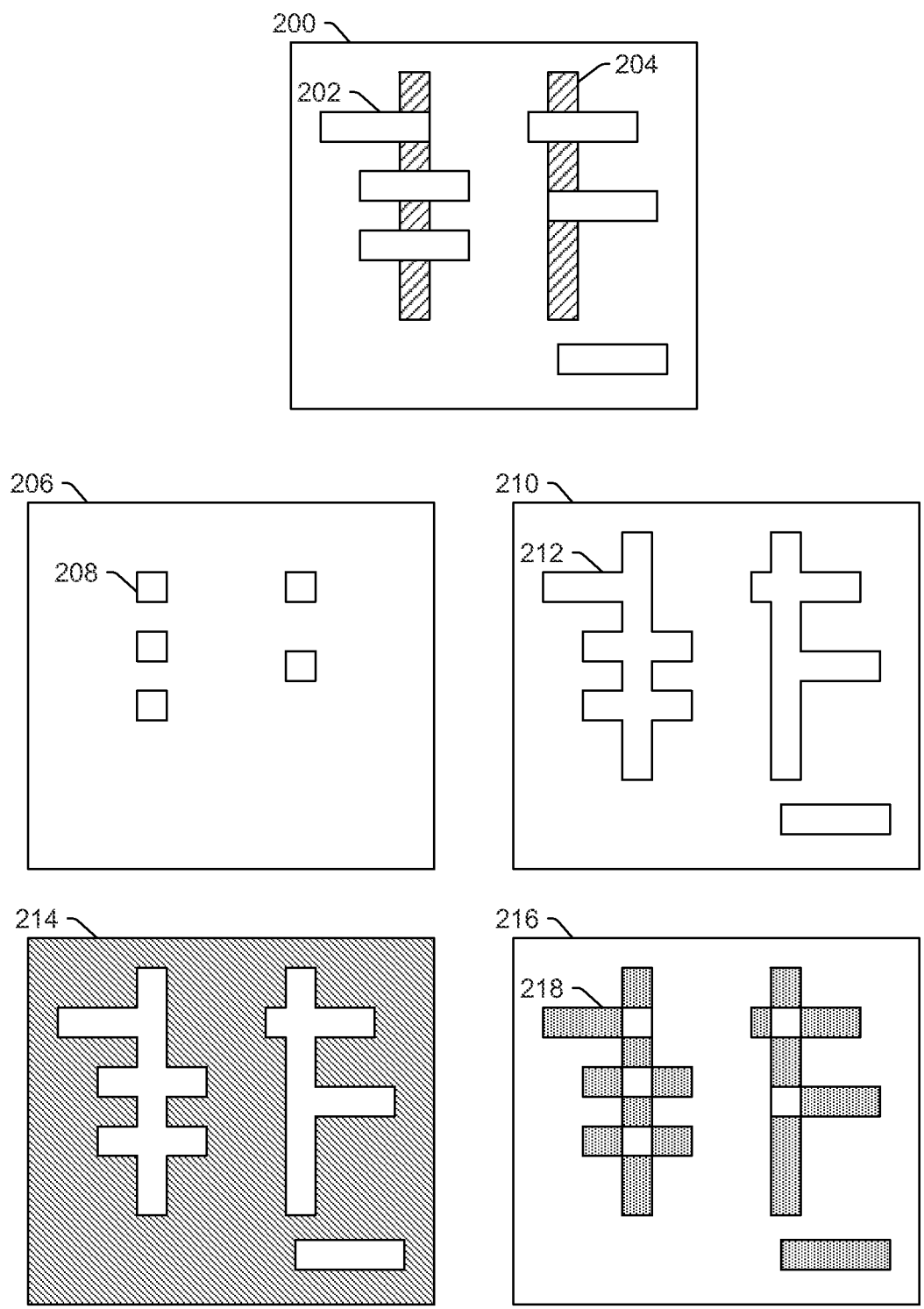
FIG. 2 is a schematic diagram illustrating one example of polygons in a design clip for two layers of a design for a wafer and results of embodiments of layer logic operations between the layers.

FIG. 2 illustrates the input and output of various logical operators on one example of polygons that generally represent polygons that may be included in design data for a generic wafer. In design clip 200, solid polygons 202 represent layer 1, and polygons 204 having diagonal lines formed therein represent layer 2. Polygons 204 include two vertically oriented lines or trenches that overlap with portions of solid polygons 202.

Also shown in FIG. 2 are the results of layer logic operations between these layers. For example, result 206 is the result of an AND operator performed for polygons 202 and 204. The result includes intersecting polygons 208 between the two layers. Result 210 is the result of an OR operator performed for polygons 202 and 204. Result 210 includes union 212 of polygons between the two layers. Result 214 is the result of a NOT operator performed for polygons 202 and 204. This result was produced by merging polygons 202 and 204 and applying an inverse on the polygons. Result 216 is the result of an XOR operator performed for polygons 202 and 204. This result was produced by finding polygons 218 that are exclusive to regions in the layers. The layer logic operators described above can be applied on one or more layers. A design attribute formula may also be based on a combination of layers such as "My new attribute"=COUNT (POLY OR ETCH OR STI), where POLY, ETCH, and STI are the polysilicon, etch, and shallow trench isolation layers of the wafer, respectively.

The dynamic design attribute formula also contains "result calculators." These calculators are basically the mathematic calculations performed on the set of resultant polygons from layer logic operations. The result of applying the "calculator" is basically the attribute value. In one embodiment, the one or more calculations include one or more of: counting a number of the polygons resulting from the one or more logical operators, counting a number of vertices in each of the polygons resulting from the one or more logical operators, summing an area of all of the polygons resulting from the one or more logical operators, determining a minimum area of all areas of the polygons resulting from the one or more logical operators, and determining a maximum area of all areas of the polygons resulting from the one or more logical operators. For example, the following result calculators may be used for the dynamic design attributes. These calculators can also be extended to support any new calculator created in the future.

a) Polygon count calculator—count the number of polygons in the result
  b) Vertex count calculator—count of the number of vertices in each polygon
  c) Polygon area calculator—sum of area of all polygons
  d) Min area calculator—minimum area of all polygon areas in the result set
  e) Max area—maximum area of all polygon areas in the result set In one embodiment, the calculated design attributes include pattern density of polygons in the design. For example, based on the above, an EBB pattern density attribute in DBB can be represented as: POLYGONAREA (LAYER1 OR LAYER2 OR LAYER3 OR LAYER . . . ). In another embodiment, the calculated design attributes include overlap ratio of polygons in two or more layers of the design. For example, an overlap ratio attribute can be represented as: POLYGONAREA (LAYER1 AND LAYER2 AND LAYER3).

Figure 3:
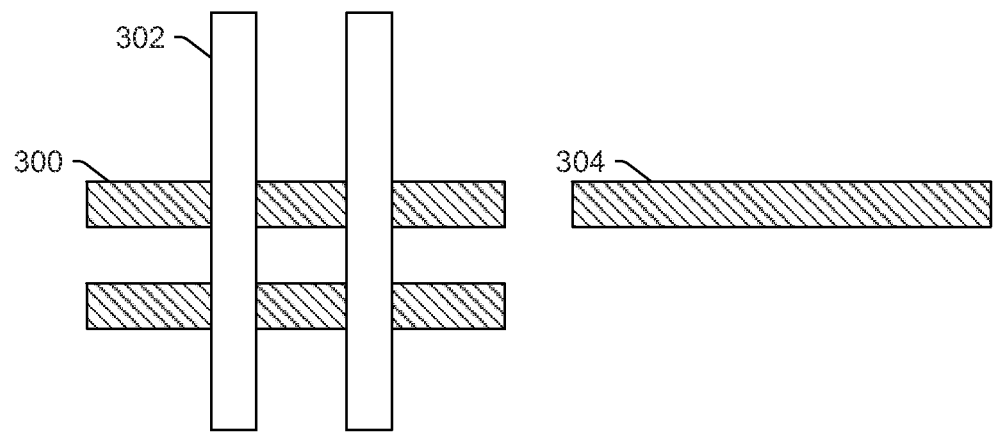
FIG. 3 is a schematic diagram illustrating one example of polygons in a design clip for two layers of a design for a wafer.

The dynamic design attributes described herein may be used for separating nuisance defects from other defects detected on wafers. For example, the attributes may be used for eliminating nuisance defects in empty areas in which no pattern is printed. This can be achieved by defining a dynamic design attribute performing an OR operation on all layers. In addition, the attributes described herein may be used for identifying dummy related nuisance defects. For example, in the design shown in FIG. 3, polygons 300 are polygons in the poly layer, and polygons 302 are polygons in the diffusion layer. If a defect lands on an area in which poly and diffusion overlap and if the overlap is greater than 90%, the defect may be considered a nuisance defect. If the defect lands on a non-overlapping area, it is considered as a real defect. For cases like this, a new dynamic design attribute with an AND operator between the layers can be defined.

The dynamic design attributes described herein may also be used for systematic defects across multiple products. For example, most systematic defects in a foundry are repetitive across multiple products in the same design rule with some variations in the pattern dimension and the patterns surrounding it. Most defect types have common rules like maximum line width, layer combination, spacing between polygons, etc., and these rules can be ported from device to device to monitor or find defect types of interest. Semiconductor IC manufacturers can create these rules, store them in a database, and use them whenever a new device is required to be ramped. Logical operators described above are possible and they can be applied based on different user scenarios. Providing flexibility in software to come up with these definitions on the fly will improve the characterization flexibility for application engineering and also identify new use cases for applying DBB.

Prompting the user for the information for the DBB process may be performed in any suitable manner. For example, a user may provide input to the wafer inspection tool that a wafer inspection recipe is to be run. In one such example, a user may select a wafer inspection recipe from a list of available wafer inspection recipes and select a run option. The list of recipes and the run option may be displayed to the user by any display device coupled to the wafer inspection tool. After the user has selected a wafer inspection recipe to run, a prompt may be displayed to the user on the display device asking if new information for a DBB process for the recipe is to be provided by the user. If the user selects an option for inputting new information, the display device may display the DBB process for the wafer inspection recipe to be run with various information about the binning process such that the user can change, delete, or add information to the existing process.

The method also includes receiving the information from the user, as shown in step 702 of FIG. 7, and updating the wafer inspection recipe based on the received information, as shown in step 704 of FIG. 7. The information may be received from the user via any' suitable input device. The wafer inspection recipe may be updated in any suitable manner. In this manner, software uses the formulae defined by the user instead of a hard-coded function in code.

The method further includes performing inspection of a wafer according to the updated wafer inspection recipe, as shown in step 706 of FIG. 7. Performing the inspection includes scanning at least a portion of the wafer with the wafer inspection tool thereby generating output responsive to light from at least the portion of the wafer, as shown in step 708 of FIG. 7, which may be performed in any suitable manner. In addition, performing the inspection includes detecting defects on the wafer based on the output, as shown in step 710 of FIG. 7, which may be performed in any suitable manner. Performing the inspection further includes binning the defects detected on the wafer according to the DBB process in the updated wafer inspection recipe, as shown in step 712 of FIG. 7, which may be performed as described further herein. The prompting, receiving, updating, performing, scanning, detecting, and binning steps are performed by the wafer inspection tool, which may be configured as described further herein.

The DBB attributes may be calculated in the main user interface (UI) during an inspection run. For example, given a defect location, inspector software has the ability to retrieve design information, or design clips, which is basically the design background around a given defect. The DBB attributes may be used in the DBB process to separate nuisance or sample shape defects of interest (DOI) using design context information. For example, in one embodiment, the binning step separates the defects that are nuisance defects into one or more first groups and the defects that are DOI into one or more second groups. In another embodiment, the binning step shapes a sample of the defects that are DOI by separating different types of the DOI into different groups.

In some embodiments, the information includes one or more layers of the wafer for which the design is used to calculate the design attributes. For example, the design clip information described above may be retrieved for specific layers. In one embodiment, one or more parameters of the DBB process are based on multi-layer design rules. For example, dynamic design attributes can enable better binning or sample shaping defects based on multi-layer design rule. The binning process may also include applying design rule check rules on the clips to better bin or separate defects based on pattern failure criticality. In one such embodiment, the binning step separates the defects into different groups having different criticalities for pattern failure by applying design rule checks on portions of design data for the wafer surrounding locations of the defects detected on the wafer.

FIG. 4 illustrates one embodiment of the method described herein. It is noted that not all of the steps shown in FIG. 4 are essential to practice of the method. Some steps may be omitted and added, and the method can still be practiced within the scope of the embodiments described herein. In addition, as will be clear to one of ordinary skill, all of the steps do not have to be performed in the order shown in FIG. 4.

Figure 4A:
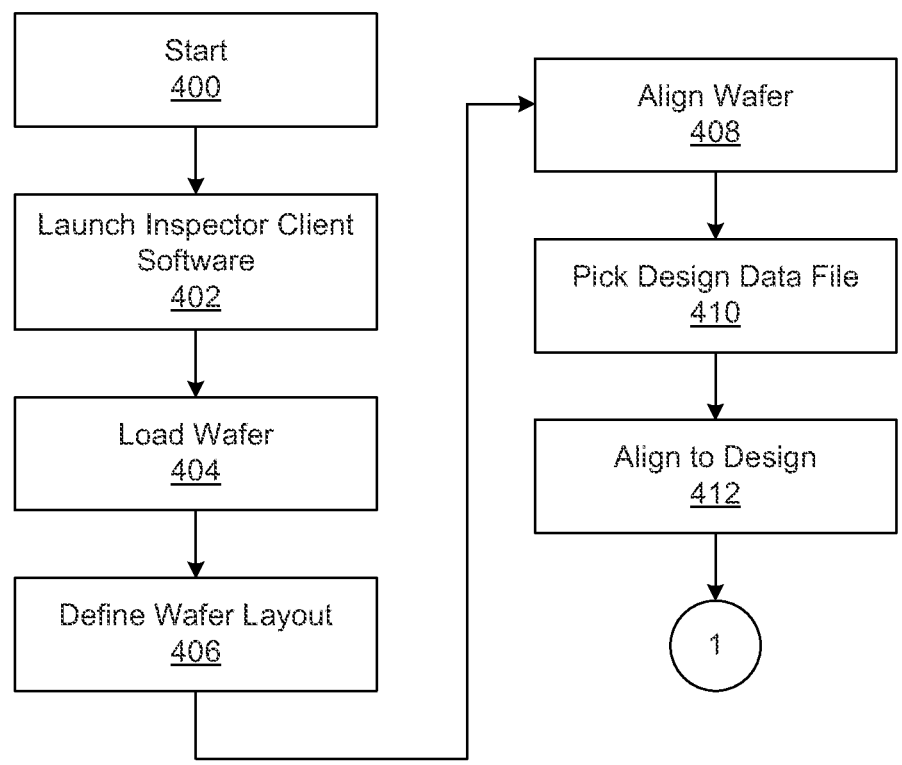
FIGS. 4a-4c are flow charts illustrating one embodiment of a method for wafer inspection.

The method starts as shown in FIG. 4a at start 400. The method includes launching inspector client software, as shown in step 402. The inspector client software is simply the software on the wafer inspection tool that is used by a user to interact with and control the inspection tool. Such software may be launched in any suitable manner. The method also includes loading a wafer, as shown in step 404. The wafer may be loaded in any suitable manner. For example, a wafer container or cassette may be loaded into the inspection tool automatically or by a user, and the user may control the wafer inspection tool to load one of the wafers from the container onto a stage of the tool.

The method further includes defining the wafer layout, as shown in step 406. Defining the wafer layout may include defining the layout of dies printed on the wafer in coordinates that are usable by the wafer inspection tool. The user may input the wafer layout using the software described above. In addition, the method includes aligning the wafer, as shown in step 408. For example, the wafer inspection tool may be configured to align the wafer within the wafer inspection tool after receiving an instruction from the user to do so.

The method may also include picking a design data file, as shown in step 410. For example, a user of the wafer inspection tool may use the software described above to select a design data file that is accessible to the wafer inspection tool. The design data file may be stored on the wafer inspection tool or may be accessible from another storage medium such as a fab database that is coupled remotely to the inspection tool. The design data file may include information for one or more layers formed or to be formed on the wafer. In addition, as shown in step 412, the method includes aligning to design. Aligning to design may include aligning the wafer or output (e.g., images) for the wafer to coordinates of the design. Aligning to design may be further performed as described in the patent to Zafar et al. incorporated by reference above.

Figure 4B:
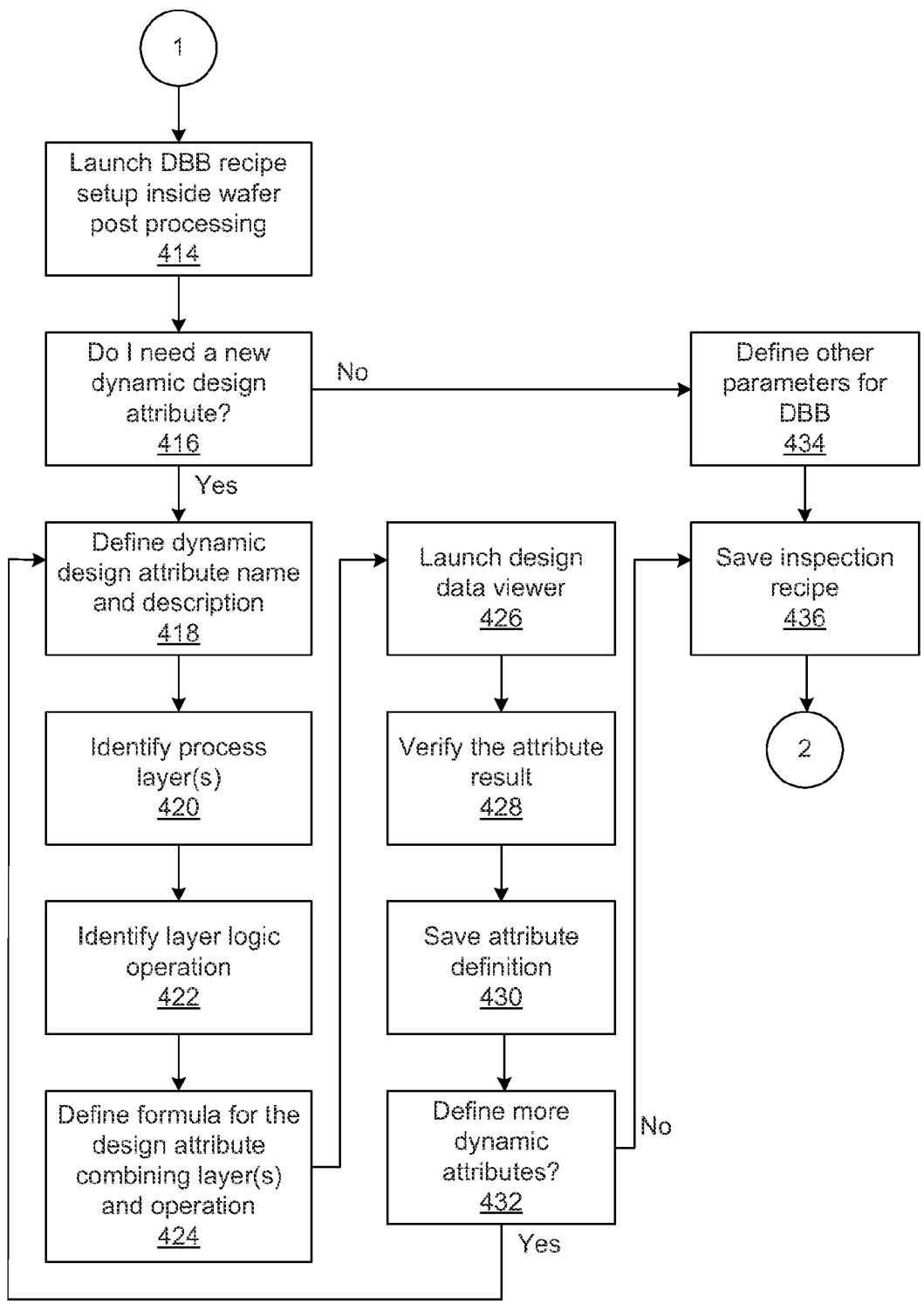

The method may then continue as shown in FIG. 4b. For example, the method may include launching DBB recipe setup inside wafer post processing, as shown in step 414. Launching the DBB recipe setup may be performed by a user via the client software described above. Step 416 of the method includes determining if a new dynamic design attribute is needed. This step may be performed by automatically querying the user if there are any new dynamic design attribute(s) when the DBB recipe setup is launched.

If the user indicates that there is a new dynamic design attribute, the method includes defining the dynamic design attribute name and description, as shown in step 418. This step may include prompting the user to input this information. The method may also include identifying the process layer(s) for the dynamic design attribute, as shown in step 420, which may also be performed by prompting the user to select or input the process layer(s). In addition, the method includes identifying the layer logic operation, as shown in step 422, which may be performed by prompting the user to select or input the layer logic operator. The method further includes defining the formula for the design attribute combining layer(s) and operator, as shown in step 424. This step may be performed by the user or automatically by the wafer inspection tool based on input from the user.

The method may then include launching a design data viewer, as shown in step 426, which may be performed by the client software described above after all of the relevant information for the new design attribute has been received from the user. The design data viewer may display to the user the relevant portion or portions of the design data that will be associated with the new design attribute. For example, the design data viewer may show each of the design clips for each of the layer(s) associated with the new design attribute. In addition, the design data viewer may show the results of the layer logic operation that would be produced for the new design attribute.

The method further includes verifying the attribute result, as shown in step 428. Verifying the attribute result may be performed by prompting the user for an indication of if the attribute result described above is satisfactory or not. The attribute result may be verified visually in the design data viewer on a sample region of the design data. In addition, the method includes saving the attribute definition, as shown in step 430. The attribute definition may be saved when a user selects a save option in the client software. The method also includes determining if more dynamic attributes are to be defined, as shown in step 432. If there are more new dynamic design attributes, the method may return to step 418 and repeat the steps between steps 418 and 432 as many times as needed.

If it is determined or indicated that there are no new dynamic design attributes in step 416, the method includes defining other parameters for DBB, as shown in step 434 of FIG. 4b. The other parameters for DBB may be input by a user via the client software described above. After the other parameters for DBB have been provided in step 434 and/or after it has been determined or indicated that there are no more new dynamic design attributes in step 432, the method may then include saving the inspection recipe, as shown in step 436. The inspection recipe may be saved in any suitable manner and in any suitable format. The inspection recipe may be stored in a storage medium located within the wafer inspection tool and/or may be stored in a storage medium that is remotely located from the wafer inspection tool (e.g., a fab database).

Figure 4C:
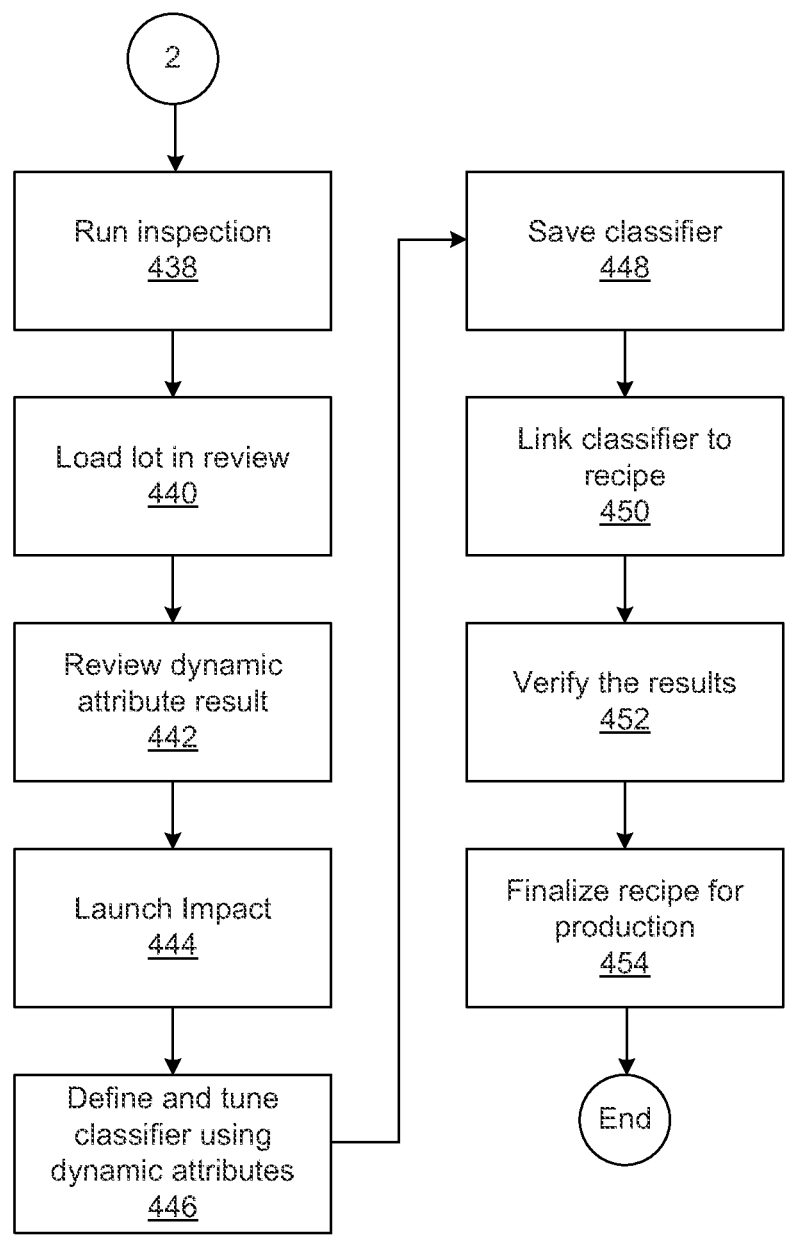

The method then continues as shown in FIG. 4c. For example, after the inspection recipe has been saved, the method includes running inspection, as shown in step 438, which may be performed in any suitable manner. The method also includes loading the lot in review, as shown in step 440. Loading the lot in review may include loading results of the inspection in a review type application on the wafer inspection tool or on a separate defect review tool such as a scanning electron microscope (SEM). In addition, the method includes reviewing the dynamic attribute result, as shown in step 442. Reviewing the dynamic attribute result may include reviewing the results in software without using the physical wafer. However, reviewing the dynamic attribute results may include revisiting locations on the physical wafer that were included in the dynamic attribute results using a defect review tool to further examine defects that were detected at the locations. In any manner, the dynamic attribute results may be reviewed to determine if any new dynamic design attributes are producing the desired results.

The method may also include launching Impact, which is defect classification software commercially available from KLA-Tencor, as shown in step 444. In place of Impact, any other suitable defect classifier software can be launched in step 444. The defect classifier can be launched from the defect review tool or the wafer inspection tool. As shown in step 446, the method includes defining and tuning the classifier using the dynamic attributes. Defining and tuning the classifier may include altering any one or more parameters of the classifier for use in the wafer inspection recipe. For example, defining and tuning the classifier may include defining and tuning a decision tree that is used in the classifier. The method also includes saving the classifier, as shown in step 448. The classifier may be stored in any suitable manner and in any suitable format. The classifier may also be stored in any of the storage media described herein (e.g., a storage medium included in the wafer inspection tool or a fab database).

The method may further include linking the classifier to the wafer inspection recipe, as shown in step 450. This step may be performed in any suitable manner. For example, a link to the classifier may be included in the wafer inspection recipe that was stored in step 436. The method also includes verifying the results, as shown in step 452, which may be performed in any suitable manner. In addition, the method includes finalizing the recipe for production, as shown in step 454, which may also be performed in any suitable manner.

Each of the embodiments of the methods described above may include any other step(s) of any other method(s) described herein. Furthermore, each of the embodiments of the methods described above may be performed by any of the systems described herein.

All of the methods described herein may include storing results of one or more steps of the method embodiments in a non-transitory computer-readable storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc. For example, after the method detects the defects, the method may include storing information about the detected defects in a storage medium.

Figure 5:
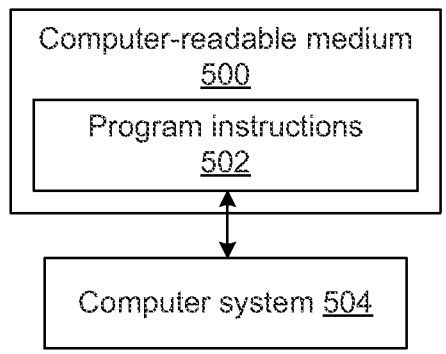
FIG. 5 is a block diagram illustrating one embodiment of a non-transitory computer-readable medium storing program instructions executable on a computer system of a wafer inspection tool for performing one or more of the computer-implemented methods described herein.

An additional embodiment relates to a non-transitory computer-readable medium storing program instructions executable on a computer system of a wafer inspection tool for performing a computer-implemented method for wafer inspection. One such embodiment is shown in FIG. 5. In particular, as shown in FIG. 5, non-transitory computer-readable medium 500 includes program instructions 502 executable on computer system 504. The computer-implemented method includes the steps of the method described above. The computer-implemented method for which the program instructions are executable may include any other step(s) described herein.

Program instructions 502 implementing methods such as those described herein may be stored on computer-readable medium 500. The computer-readable medium may be a storage medium such as a magnetic or optical disk, a magnetic tape, or any other suitable non-transitory computer-readable medium known in the art.

The program instructions may be implemented in any of various ways, including procedure-based techniques, component-based techniques, and/or object-oriented techniques, among others. For example, the program instructions may be implemented using ActiveX controls, C++ objects, JavaBeans, Microsoft Foundation Classes ("MFC"), or other technologies or methodologies, as desired.

The computer system may take various forms, including a personal computer system, image computer, mainframe computer system, workstation, network appliance, Internet appliance, or other device. In general, the term "computer system" may be broadly defined to encompass any device having one or more processors, which executes instructions from a memory medium. The computer system may also include any suitable processor known in the art such as a parallel processor. In addition, the computer system may include a computer platform with high speed processing and software, either as a standalone or a networked tool.

Figure 6:
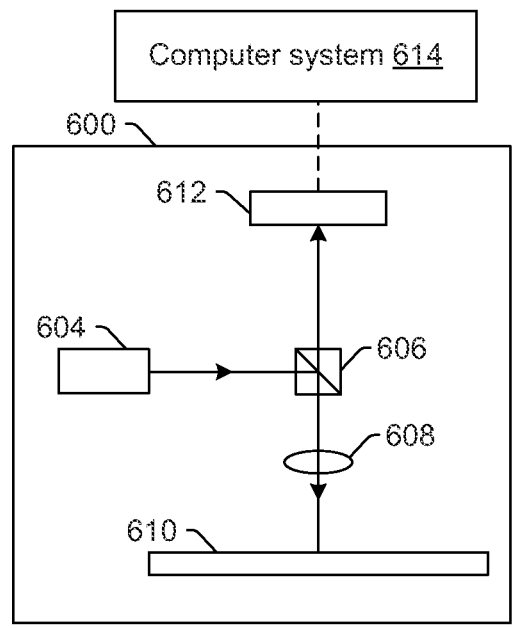
FIG. 6 is a schematic diagram illustrating a side view of one embodiment of a wafer inspection tool.

Another embodiment relates to a wafer inspection tool. One embodiment of such a tool is shown in FIG. 6. The wafer inspection tool includes an optical subsystem configured to scan at least a portion of a wafer thereby generating output responsive to light from at least the portion of the wafer. For example, as shown in FIG. 6, the wafer inspection tool includes optical subsystem 600.

As shown in FIG. 6, the optical subsystem includes light source 604. Light source 604 may include any suitable light source known in the art such as a broadband plasma light source. In this manner, the inspection system may be configured as a broadband plasma inspection system. Light source 604 is configured to direct light to beam splitter 606, which is configured to reflect the light from light source 604 to refractive optical element 608. Refractive optical element 608 is configured to focus light from beam splitter 606 to wafer 610. Beam splitter 606 may include any suitable beam splitter such as a 50/50 beam splitter. Refractive optical element 608 may include any suitable refractive optical element, and although refractive optical element 608 is shown in FIG. 6 as a single refractive optical element, it may be replaced with one or more refractive optical elements and/or one or more reflective optical elements.

Light source 604, beam splitter 606, and refractive optical element 608 may, therefore, form an illumination channel for the optical subsystem. The illumination channel may include any other suitable elements (not shown in FIG. 6) such as one or more polarizing components and one or more filters such as spectral filters. As shown in FIG. 6, the light source, beam splitter, and refractive optical element are configured such that the light is directed to the wafer at a normal or substantially normal angle of incidence. However, the light may be directed to the wafer at any other suitable angle of incidence.

The optical subsystem may be configured to scan the light over the wafer in any suitable manner.

Light reflected from wafer 610 due to illumination may be collected by refractive optical element 608 and directed through beam splitter 606 to detector 612. Therefore, the refractive optical element, beam splitter, and detector may form a detection channel of the optical subsystem. The detector may include any suitable imaging detector known in the art such as a charge coupled device (CCD). This detection channel may also include one or more additional components (not shown in FIG. 6) such as one or more polarizing components, one or more spatial filters, one or more spectral filters, and the like. Detector 612 is configured to generate output that is responsive to the reflected light detected by the detector. The output may include signals, signal data, images, image data, and any other suitable output.

As described above, the detector included in the optical subsystem may be configured to detect light reflected from the wafer. Therefore, the detection channel included in the optical subsystem may be configured as a bright field (BF) channel. However, the optical subsystem may include one or more detection channels (not shown) that may be used to detect light scattered from the wafer due to illumination of the wafer. In addition, one or more parameters of the detection channel shown in FIG. 6 may be altered such that the detection channel detects light scattered from the wafer. In this manner, the optical subsystem may be configured as a dark field (DF) tool and/or a BF tool.

The wafer inspection tool also includes a computer subsystem coupled to the optical subsystem. For example, the computer subsystem may be coupled to a detector of the optical subsystem. In one such example, as shown in FIG. 6, computer system 614 is coupled to detector 612 of optical subsystem 600 (e.g., by one or more transmission media shown by the dashed lines in FIG. 6, which may include any suitable transmission media known in the art). The computer system may be coupled to the detector in any suitable manner. The computer system may be coupled to the optical subsystem in any other suitable manner such that image(s) and any other information for the wafer generated by the optical subsystem can be sent to the computer system and, optionally, such that the computer system can send instructions to the optical subsystem to perform one or more steps described herein.

Computer system 614 is configured for, at run time of a wafer inspection recipe, prompting a user of the wafer inspection tool on which the wafer inspection recipe is performed for information for a DBB process. The information includes one or more formulae for calculating design attributes from a design for the wafer. The design attributes are used to bin the defects in the DBB process. The computer system is also configured for receiving information from the user. In addition, the computer system is configured for updating the wafer inspection recipe based on the received information. The computer system is further configured for detecting defects on the wafer based on the output and binning the defects detected on the wafer according to the DBB process in the updated wafer inspection recipe. Each of these steps may be performed as described further herein. In addition, the computer system may be configured to perform any other step(s) described herein. The wafer inspection tool shown in FIG. 6 may be further configured as described herein.

It is noted that FIG. 6 is provided herein to generally illustrate one configuration of an optical subsystem that may be included in the wafer inspection tool embodiments described herein. Obviously, the configuration of the optical subsystem described herein may be altered to optimize the performance of the tool as is normally performed when designing a commercial inspection tool. In addition, the wafer inspection tools described herein may be implemented using an existing optical subsystem (e.g., by adding functionality described herein to an existing inspection tool) such as the 28XX, 29XX, and Puma 9XXX series of tools that are commercially available from KLA-Tencor, Milpitas, Calif. For some such tools, the methods described herein may be provided as optional functionality of the tool (e.g., in addition to other functionality of the tool). Alternatively, the wafer inspection tools described herein may be designed "from scratch" to provide a completely new tool.

Further modifications and alternative embodiments of various aspects of the invention will be apparent to those skilled in the art in view of this description. For example, methods and systems for dynamic design attributes for wafer inspection are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method for wafer inspection, comprising:
   at run time of a wafer inspection recipe, prompting a user of a wafer inspection tool on which the wafer inspection recipe is performed for information for a design based binning process, wherein the information comprises one or more formulae for calculating design attributes from a design for a wafer, wherein the calculated design attributes comprise overlap ratio of polygons in two or more layers of the design, and wherein the design attributes are used to bin the defects in the design based binning process;
   receiving the information from the user;
   updating the wafer inspection recipe based on the received information; and
   performing inspection of the wafer according to the updated wafer inspection recipe, wherein said performing comprises:
      scanning the wafer with the wafer inspection tool thereby generating output responsive to light from the wafer;
      detecting defects on the wafer based on the output; and
      binning the defects detected on the wafer according to the design based binning process in the updated wafer inspection recipe, wherein the prompting, receiving, updating, performing, scanning, detecting, and binning steps are performed by the wafer inspection tool.

2. The method of claim 1, wherein the one or more formulae comprise one or more formulae for calculating the design attributes from design data for the design surrounding locations of the defects detected on the wafer.

3. The method of claim 1, wherein the information comprises one or more layers of the wafer for which the design is used to calculate the design attributes.

4. The method of claim 1, wherein one or more parameters of the design based binning process are based on multi-layer design rules.

5. The method of claim 1, wherein the binning step separates the defects into different groups having different criticalities for pattern failure by applying design rule checks on design data for the wafer surrounding locations of the defects detected on the wafer.

6. The method of claim 1, wherein the binning step separates the defects that are nuisance defects into one or more first groups and the defects that are defects of interest into one or more second groups.

7. The method of claim 1, wherein the binning step shapes a sample of the defects that are defects of interest by separating different types of the defects of interest into different groups.

8. The method of claim 1, wherein the information further comprises flags for each of the design attributes indicating whether the design attributes are categorical attributes or measurement attributes.

9. The method of claim 1, wherein the binning step separates the defects based on design data for the wafer surrounding locations of the defects detected on the wafer, and wherein the information further comprises flags for each of the design attributes indicating an extent of the design data used to calculate the design attributes.

10. The method of claim 9, wherein the extent of the design data are an entirety of the design data or an area of interest within the design data.

11. The method of claim 1, wherein the information further comprises one or more layer operators for the one or more formulae, and wherein the one or more layer operators are one or more logical operators applied to polygons of two or more layers in the design.

12. The method of claim 11, wherein the one or more logical operators comprise one or more of logical AND, OR, XOR, and NOT operators.

13. The method of claim 11, wherein the information further comprises one or more calculations for the one or more formulae performed on polygons resulting from the one or more logical operators, and wherein the results of the one or more calculations are the calculated design attributes.

14. The method of claim 13, wherein the one or more calculations comprise one or more of: counting a number of the polygons resulting from the one or more logical operators, counting a number of vertices in each of the polygons resulting from the one or more logical operators, summing an area of all of the polygons resulting from the one or more logical operators, determining a minimum area of all areas of the polygons resulting from the one or more logical operators, and determining a maximum area of all areas of the polygons resulting from the one or more logical operators.

15. The method of claim 1, wherein the calculated design attributes further comprise pattern density of polygons in the design.

16. The method of claim 1, wherein the wafer inspection tool is configured as a broadband plasma tool.

17. A non-transitory computer-readable medium, storing program instructions executable on a computer system of a wafer inspection tool for performing a computer-implemented method for wafer inspection, wherein the computer-implemented method comprises:
at run time of a wafer inspection recipe, prompting a user of the wafer inspection tool on which the wafer inspection recipe is performed for information for a design based binning process, wherein the information comprises one or more formulae for calculating design attributes from a design for the wafer, wherein the calculated design attributes comprise overlap ratio of polygons in two or more layers of the design, and wherein the design attributes are used to bin the defects in the design based binning process;
receiving the information from the user;
updating the wafer inspection recipe based on the received information; and
performing inspection of the wafer according to the updated wafer inspection recipe, wherein said performing comprises:
scanning the wafer with the wafer inspection tool thereby generating output responsive to light from the wafer;
detecting defects on the wafer based on the output; and
binning the defects detected on the wafer according to the design based binning process in the updated wafer inspection recipe.

18. A wafer inspection tool, comprising:
an optical subsystem configured to scan a wafer thereby generating output responsive to light from the wafer; and
a computer subsystem configured for:
at run time of a wafer inspection recipe, prompting a user of the wafer inspection tool on which the wafer inspection recipe is performed for information for a design based binning process, wherein the information comprises one or more formulae for calculating design attributes from a design for the wafer, wherein the calculated design attributes comprise overlap ratio of polygons in two or more layers of the design, and wherein the design attributes are used to bin the defects in the design based binning process;
receiving the information from the user;
updating the wafer inspection recipe based on the received information;
detecting defects on the wafer based on the output; and
binning the defects detected on the wafer according to the design based binning process in the updated wafer inspection recipe.

19. The wafer inspection tool of claim 18, wherein the one or more formulae comprise one or more formulae for calculating the design attributes from design data for the design surrounding locations of the defects detected on the wafer.

20. The wafer inspection tool of claim 18, wherein the information comprises one or more layers of the wafer for which the design is used to calculate the design attributes.

21. The wafer inspection tool of claim 18, wherein one or more parameters of the design based binning process a based on multi-layer design rules.

22. The wafer inspection tool of claim 18, wherein the binning step separates the defects into different groups having different criticalities for pattern failure by applying design rule checks on design data for the wafer surrounding locations of the defects detected on the wafer.

23. The wafer inspection tool of claim 18, wherein the binning step separates the defects that are nuisance defects into one or more first groups and the defects that are defects of interest into one or more second groups.

24. The wafer inspection tool of claim 18, wherein the binning step shapes a sample of the defects that are defects of interest by separating different types of the defects of interest into different groups.

25. The wafer inspection tool of claim 18, wherein the information further comprises flags for each of the design attributes indicating whether the design attributes are categorical attributes or measurement attributes.

26. The wafer inspection tool of claim 18, wherein the binning step separates the defects based on design data for the water surrounding locations of the defects detected on the wafer, and wherein the information further comprises flags for each of the design attributes indicating an extent of the design data used to calculate the design attributes.

27. The wafer inspection tool of claim 26, wherein the extent of the design data are an entirety of the design data or an area of interest within the design data.

28. The wafer inspection tool of claim 18, wherein the information further comprises one or more layer operators for the one or more formulae, and wherein the one or more layer operators are one or more logical operators applied to polygons of two or more layers in the design.

29. The wafer inspection tool of claim 28, wherein the one or more logical operators comprise one or more of logical AND, OR, XOR, and NOT operators.

30. The wafer inspection tool of claim 28, wherein the information further comprises one or more calculations for the one or more formulae performed on polygons resulting from the one or more logical operators, and wherein the results of the one or more calculations are the calculated design attributes.

31. The wafer inspection tool of claim 30, wherein the one or more calculations comprise one or more of counting a number of the polygons resulting from the one or more logical operators, counting a number of vertices in each of the polygons resulting from the one or more logical operators, summing an area of all of the polygons resulting from the one or more logical operators, determining a minimum area of all areas of the polygons resulting from the one or more logical operators, and determining a maximum area of all areas of the polygons resulting from the one or more logical operators.

32. The wafer inspection tool of claim 18, wherein the calculated design attributes further comprise pattern density of polygons in the design.

33. The wafer inspection tool of claim 18, wherein the wafer inspection tool is configured as a broadband plasma tool.

* * * * *